United States Patent
Sood

(10) Patent No.: US 8,257,716 B2
(45) Date of Patent: Sep. 4, 2012

(54) ANTI-PDEF ANTIBODIES AND USES THEREOF

(76) Inventor: Ashwani Sood, Williamsville, NY (US)

( * ) Notice: Subject to any disclaimer, the term of this patent is extended or adjusted under 35 U.S.C. 154(b) by 211 days.

(21) Appl. No.: 12/342,037

(22) Filed: Dec. 22, 2008

(65) Prior Publication Data

US 2009/0202595 A1 Aug. 13, 2009

Related U.S. Application Data

(60) Provisional application No. 61/015,925, filed on Dec. 21, 2007.

(51) Int. Cl.
| | |
|---|---|
| A61K 39/00 | (2006.01) |
| A61K 39/395 | (2006.01) |
| A61K 49/00 | (2006.01) |
| C12N 5/07 | (2010.01) |
| C12N 5/16 | (2006.01) |

(52) U.S. Cl. ........... 424/277.1; 424/138.1; 424/155.1; 424/9.2; 435/344; 435/330

(58) Field of Classification Search ............... None
See application file for complete search history.

(56) References Cited

U.S. PATENT DOCUMENTS

| | | | |
|---|---|---|---|
| 6,265,565 B1 * | 7/2001 | Bandman et al. | ........... 536/23.5 |
| 2001/0010934 A1 * | 8/2001 | Libermann et al. | ........... 435/325 |
| 2004/0197345 A1 | 10/2004 | Libermann et al. | |

OTHER PUBLICATIONS

Doria-Rose et al., Methods, 2003; 31:207-216.*
NCBI Accession No. NM_012391 (2000) (updated May 16, 2010).
Feldman et al., Cancer Research 63:4626-4631 (2003).
Ghadersohi et al., Clinical Cancer Research 7:2731-2738 (2001).
Ghadersohi et al., Breast Cancer Res. Treat. 102:19-30 (2007).
Ghadersohi et al., Int. J. Cancer 123:1376-1384 (2008).
Gu et al., Cancer Research 67:4219-4226 (2007).
Nozawa et al., Cancer Research 60:1348-1352 (2000).
Oettgen et al., J. Biol. Chem. 275:12.16-1225 (2000).
Rodabaugh et al., Int. J. Gynecol. Pathol. 26:10-15 (2007).
Sood et al., Hum. Pathol. 38:1628-1638 (2007).
Turcotte et al., Neoplasia 9:788-796 (2007).

* cited by examiner

Primary Examiner — Doug Schultz
(74) Attorney, Agent, or Firm — Heslin Rothenberg Farley & Mesiti P.C.; Andrew K. Gonsalves

(57) ABSTRACT

The present invention relates to an isolated antibody or antigen-binding fragment thereof that specifically binds with high affinity to at least a portion of a segment of human prostate-derived Ets transcription factor (PDEF). The anti-PDEF antibody of the present invention is effective in prognostic and diagnostic assays for detecting PDEF with immunohistochemistry. The present invention also relates to methods of making the anti-PDEF antibody disclosed herein. The present invention further relates to vaccines against cancers associated with positive expression of PDEF, as well as methods for treating those cancers. Vectors, diagnostic kits, and hybridomas are also disclosed.

1 Claim, 20 Drawing Sheets

FIG. 1A

Significant sequences homology alignments with PDEF-1-104 segment:

| Sequence | Score | Homologous region | %Homology |
|---|---|---|---|
| PDEF | 207 | 1-104 | 100 |

FIG. 1B

Significant sequence homology alignments with PDEF pointed domain

| Sequence | Score | Homologous region | % Homology |
|---|---|---|---|
| PDEF | 150 | 141-210 | 100 |
| Tel2 Human | 53 | 141-210 | 56 |
| Erg Human | 52 | 141-206 | 62 |
| ETV-6 Human | 52 | 146-203 | 63 |
| ETV-7 Human | 53 | 146-210 | 56 |
| Ets1 Human | 43 | 142-208 | 57 |
| Ets2 Human | 37 | 142-207 | 54 |
| ELF-5 Human | 36 | 143-203 | 56 |
| FLI-1 Human | 45 | 142-210 | 58 |
| GABPA Human | 49 | 142-210 | 60 |

FIG. 1C

Significant sequences homology alignments with PDEF Ets Domain*

| Sequence | Score | Homologous region | % Homology |
| --- | --- | --- | --- |
| PDEF | 176 | 248-331 | 100 |
| Elf-2 Human | 97 | 250-331 | 74 |
| Elf-1 Human | 97 | 249-331 | 72 |
| Elf-4 Human | 96 | 249-331 | 74 |
| ELK-1 Human | 92 | 249-331 | 69 |
| ESE-2 Human | 84 | 250-331 | 69 |
| EHF Human | 82 | 250-331 | 74 |
| ESE-3 Human | 80 | 250-331 | 68 |
| ETV-4 Human | 84 | 249-331 | 69 |
| Ets2 Human | 80 | 248-331 | 61 |
| Ets1 Human | 78 | 248-331 | 61 |
| ETV-6 Human | 75 | 251-331 | 66 |
| ERG Human | 71 | 249-331 | 60 |
| FLI-1 Human | 70 | 249-331 | 60 |
| GABP Human | 70 | 249-331 | 60 |
| SPI1 Human | 54 | 249-331 | 60 |

FIG. 1D

Significant sequence homology alignment with PDEF-105-141 segment

| Sequence | Score | Homology region | % Homology |
| --- | --- | --- | --- |
| PDEF | 78 | 105-141 | 100 |

FIG. 1E

Significant sequence homology alignment with PDEF-214-247 segment

| Sequence | Score | Homology region | % Homology |
| --- | --- | --- | --- |
| PDEF | 74 | 214-247 | 100 |

*Only proteins with 60% or higher homology with PDEF in this domain are shown

Panel A      Panel B

Panel C      Panel D

Normal prostate　　　　　　　　　　　Normal Bronchus

Benign

Tumor

Benign

Tumor

```
                          SEQUENCE LISTING

<160> NUMBER OF SEQ ID NOS: 4

<210> SEQ ID NO 1
<211> LENGTH: 335
<212> TYPE: PRT
<213> ORGANISM: Homo sapiens

<400> SEQUENCE: 1

Met Gly Ser Ala Ser Pro Gly Leu Ser Ser Val Ser Pro Ser His Leu
1               5                   10                  15

Leu Leu Pro Pro Asp Thr Val Ser Arg Thr Gly Leu Glu Lys Ala Ala
                20                  25                  30

Ala Gly Ala Val Gly Leu Glu Arg Arg Asp Trp Ser Pro Ser Pro Pro
            35                  40                  45

Ala Thr Pro Glu Gln Gly Leu Ser Ala Phe Tyr Leu Ser Tyr Phe Asp
        50                  55                  60

Met Leu Tyr Pro Glu Asp Ser Ser Trp Ala Ala Lys Ala Pro Gly Ala
65                  70                  75                  80

Ser Ser Arg Glu Glu Pro Pro Glu Glu Pro Glu Gln Cys Pro Val Ile
                85                  90                  95

Asp Ser Gln Ala Pro Ala Gly Ser Leu Asp Leu Val Pro Gly Gly Leu
                100                 105                 110

Thr Leu Glu Glu His Ser Leu Glu Gln Val Gln Ser Met Val Val Gly
            115                 120                 125

Glu Val Leu Lys Asp Ile Glu Thr Ala Cys Lys Leu Leu Asn Ile Thr
        130                 135                 140

Ala Asp Pro Met Asp Trp Ser Pro Ser Asn Val Gln Lys Trp Leu Leu
145                 150                 155                 160

Trp Thr Glu His Gln Tyr Arg Leu Pro Pro Met Gly Lys Ala Phe Gln
                165                 170                 175

Glu Leu Ala Gly Lys Glu Leu Cys Ala Met Ser Glu Glu Gln Phe Arg
            180                 185                 190

Gln Arg Ser Pro Leu Gly Gly Asp Val Leu His Ala His Leu Asp Ile
        195                 200                 205

Trp Lys Ser Ala Ala Trp Met Lys Glu Arg Thr Ser Pro Gly Ala Ile
    210                 215                 220

His Tyr Cys Ala Ser Thr Ser Glu Glu Ser Trp Thr Asp Ser Glu Val
225                 230                 235                 240

Asp Ser Ser Cys Ser Gly Gln Pro Ile His Leu Trp Gln Phe Leu Lys
                245                 250                 255

Glu Leu Leu Leu Lys Pro His Ser Tyr Gly Arg Phe Ile Arg Trp Leu
            260                 265                 270

Asn Lys Glu Lys Gly Ile Phe Lys Ile Glu Asp Ser Ala Gln Val Ala
        275                 280                 285
```

```
Arg Leu Trp Gly Ile Arg Lys Asn Arg Pro Ala Met Asn Tyr Asp Lys
    290                 295                 300
Leu Ser Arg Ser Ile Arg Gln Tyr Tyr Lys Lys Gly Ile Ile Arg Lys
305                 310                 315                 320
Pro Asp Ile Ser Gln Arg Leu Val Tyr Gln Phe Val His Pro Ile
                325                 330                 335

<210> SEQ ID NO 2
<211> LENGTH: 104
<212> TYPE: PRT
<213> ORGANISM: Homo sapiens

<400> SEQUENCE: 2

Met Gly Ser Ala Ser Pro Gly Leu Ser Val Ser Pro Ser His Leu
1               5                   10                  15
Leu Leu Pro Pro Asp Thr Val Ser Arg Thr Gly Leu Glu Lys Ala Ala
                20                  25                  30
Ala Gly Ala Val Gly Leu Glu Arg Arg Asp Trp Ser Pro Ser Pro Pro
            35                  40                  45
Ala Thr Pro Glu Gln Gly Leu Ser Ala Phe Tyr Leu Ser Tyr Phe Asp
        50                  55                  60
Met Leu Tyr Pro Glu Asp Ser Ser Trp Ala Ala Lys Ala Pro Gly Ala
65                  70                  75                  80
Ser Ser Arg Glu Glu Pro Pro Glu Glu Pro Gln Cys Pro Val Ile
                85                  90                  95
Asp Ser Gln Ala Pro Ala Gly Ser
            100

<210> SEQ ID NO 3
<211> LENGTH: 37
<212> TYPE: PRT
<213> ORGANISM: Homo sapiens

<400> SEQUENCE: 3

Leu Asp Leu Val Pro Gly Gly Leu Thr Leu Glu His Ser Leu Glu
1               5                   10                  15
Gln Val Gln Ser Met Val Val Gly Glu Val Leu Lys Asp Ile Glu Thr
                20                  25                  30
Ala Cys Lys Leu Leu
        35

<210> SEQ ID NO 4
<211> LENGTH: 37
<212> TYPE: PRT
<213> ORGANISM: Homo sapiens

<400> SEQUENCE: 4

Ser Ala Ala Trp Met Lys Glu Arg Thr Ser Pro Gly Ala Ile His Tyr
1               5                   10                  15
Cys Ala Ser Thr Ser Glu Glu Ser Trp Thr Asp Ser Glu Val Asp Ser
                20                  25                  30
Ser Cys Ser Gly Gln
        35
```

ANTI-PDEF ANTIBODIES AND USES THEREOF

CROSS-REFERENCE TO RELATED APPLICATIONS

This application claims the benefit of U.S. Provisional Patent Application Ser. No. 61/015,925, filed Dec. 21, 2007, which is hereby incorporated by reference herein in its entirety.

GOVERNMENT RIGHTS STATEMENT

The present invention was made with U.S. Government support under National Cancer Institute Grant No. CA86164 and Department of Defense Grant No. BC045095. The U.S. Government has certain rights in the invention.

FIELD OF THE INVENTION

The present invention relates to an isolated antibody or antigen-binding fragment thereof that specifically binds with high affinity to at least a portion of a segment of human prostate-derived Ets transcription factor (PDEF). The present invention also relates to vaccines, vectors, and methods of using the anti-PDEF antibody in prognostic and diagnostic methods.

BACKGROUND OF THE INVENTION

As used herein, certain citations to references are indicated as numerals or alphanumerical symbols in parentheticals, and are further described in the "References Cited" listing contained herein.

Breast cancer is the most common malignancy in women, as about a million new cases of this cancer are diagnosed worldwide each year, and 375,000 women die from it (B1). Although early detection through screening mammography has increased the proportion of in situ and early stage breast cancers that have excellent prognosis, mortality rates from recurrent and late stage breast cancers have not declined significantly (B2). Consequently, conventional therapies including surgery, radiation and chemotherapy need to be supplemented with novel therapies that translate into significant improvement in the clinical outcome for most breast cancer patients.

Similarly, prostate cancer is the most commonly diagnosed malignancy in men, with about 220,000 new cases of prostate cancer diagnosed each year in the U.S. alone. Of these, approximately two-thirds are treated by surgery or radiation therapy, and 40% of the treated men will eventually relapse, as characterized by rising levels of prostate specific antigen (B3, B4). Relapsed advanced and metastatic prostate cancer remains the primary cause of death from this cancer, since current systemic hormonal and chemotherapy approaches are only marginally successful (B5). Consequently there is an urgent need for novel therapies to treat advanced prostate cancer.

Further, despite intense therapeutic efforts, ovarian cancer remains the fifth leading cause of death among women in the United States (B6). Serous adenocarcinomas account for approximately 80% of all ovarian cancers and are considered surface epithelial tumors (B7). Early stage epithelial ovarian cancer has an excellent prognosis with 5 year survival rates above 90%. However, about 80% of patients with ovarian cancer initially present with metastatic disease, resulting in 5 year survival rates of only 10-20%. Following primary therapy, as many as 70% of women with advanced ovarian cancer will experience a recurrence of their disease. Novel therapies to eradicate the residual or recurrent malignancy are critically needed to increase the unacceptable low survival rates (B8).

Prostate derived Ets factor (PDEF) belongs to the Ets family of transcription factors that play an important role in normal as well as neoplastic development (B9-B13). However, despite such promise, knowledge in the art about the characteristics of PDEF expression in human cancer remains limited.

PDEF was originally described as a novel prostate specific transcription factor based on its prostate restricted expression in normal human tissues and its ability to induce the expression of prostate specific antigen (PSA) in tumor cell lines (A1). Shortly thereafter, it was shown that (i) PDEF mRNA was frequently over expressed in primary breast tumors from patients, and (ii) among normal tissues, it showed expression in the trachea/bronchus tissues in addition to the normal prostate tissue (A2). In contrast, other normal tissues including brain, heart, kidney, liver, lung, skeletal muscle, spleen, testis, and uterus were negative for PDEF expression (A2). More recently, a screen of a much larger collection of breast tumors and normal human tissues has confirmed the Inventor's findings and showed that roughly 75% of newly diagnosed breast tumors show varying level of over expression of PDEF (A3). These observations suggested a role for PDEF in breast and prostate cancer progression.

A major deficiency of the above studies was that all the work was performed at the PDEF mRNA level, and in the absence of any evidence showing correspondence between PDEF mRNA and PDEF protein expression, a putative role for PDEF in tumor progression remained speculative, at best. Moreover, two groups prepared antibodies against the full-length PDEF protein and reported that PDEF protein was strongly expressed in normal breast (A4) and prostate (A5) tissues, but only weakly in the tumor tissues. The latter results were diametrically opposite to those reported for PDEF mRNA (A1-3). One explanation for such discrepant reports of PDEF mRNA and protein expression was that the antibodies to full-length PDEF proteins were not specific for PDEF, and may be cross-reacting with other members of the Ets transcription factor family to which PDEF belongs. Specifically, there are two structural motifs within the sequence of PDEF, called "Pointed domain" and DNA binding "Ets" domain, and these show high level of sequence homology with similar structural motifs present in other members of the Ets factor family (FIG. 1), and these appeared likely as targets for cross-reaction with anti-PDEF antibodies.

One approach to investigating PDEF has involved the attempt to develop antibodies with the bind specifically to PDEF with high affinity. However, prior to the present invention, no such high affinity anti-PDEF antibody had been described that could be used for clinical diagnostics. For example, previously, anti-PDEF antibodies have been generated against the full-length PDEF protein (4). While these antibodies reacted with PDEF in the Western blot assay, the specificity of their reactivity in the immunohistochemistry assay for screening PDEF expression in patient's samples has remained suspect; since those antibodies reacted strongly with normal breast tissues and weakly with breast tumors tissue, a finding contradictory to previously reported PDEF mRNA expression data (3, 22, A3). A likely explanation for such uncharacteristic reactivity of antibodies against full-length PDEF is the homology between PDEF and other Ets factors in the Pointed domain and DNA binding Ets domain (see FIGS. 1B and 1C respectively). Such high degree of homology within these domains suggested the potential for cross-reaction of the antibodies with other members of the Ets transcription factor family. In fact, the Inventor's lab also previously prepared antibody against the full-length PDEF protein and found that it reacted uncharacteristically strongly with normal breast tissue.

Antibodies to fragments of PDEF have also been described, but none of these antibodies was shown to have high affinity to PDEF. For example, antibodies to amino acid residues 1-104 of PDEF were described by Ghadersohi et al. (A7, A8). However, like previously reported antibodies to full-length PDEF, the antibodies described by Ghadersohi et al. also reacted strongly with normal breast and ovarian tissues, and weakly or not at all with tumor tissues, showing a lack of specificity for PDEF in the immunohistochemical assay.

It is shown that about 80% of primary breast tumors, 70% of primary prostate tumors, and 30 to 35% of primary ovarian tumors show over-expression of PDEF protein in tumor tissues in comparison to normal tissues (1, 2). Further, (i) transfection of PDEF into a low-malignancy breast epithelial cell line induced its accelerated tumor growth in vivo in immunodeficient mice; and (ii) meta analysis of the GEO and Oncomine databases that contain the global gene expression data from breast tumors and the linked clinical outcome data for patients showed that high PDEF expression correlates with poor overall survival for patients with estrogen receptor-positive ($ER^+$) breast tumors. In prostate cancer as well, high PDEF expression was found to correlate with early biochemical PSA failure, a surrogate marker of cancer recurrence and disease progression.

Despite considerable progress in early detection of breast and prostate cancers, mortality from advanced and metastatic disease has not declined significantly over the past several decades. Further, even with the knowledge of PDEF's role in various types of cancers, prognostic, diagnostic, and treatment methods that directed to detection of PDEF or blocking of PDEF have not been forthcoming.

The present invention is directed to the deficiencies in the art.

SUMMARY OF THE INVENTION

In one aspect, the present invention relates to an isolated antibody or antigen-binding fragment thereof that specifically binds with high affinity to at least a portion of a segment of a human prostate-derived Ets transcription factor (referred to herein as "PDEF"). Suitable segments of PDEF can include, but are not limited to, the following: (i) amino acid residues 1-104 of SEQ ID NO:1; (ii) amino acid residues 105-141 of SEQ ID NO:1; or (iii) amino acid residues 214-247 of SEQ ID NO:1.

In another aspect, the present invention relates to a hybridoma that produces the antibody according to the present invention, particularly an antibody of the present invention where the antibody is a monoclonal antibody.

In yet another aspect, the present invention relates to a diagnostic kit. This kit can include, without limitation: (i) a first container containing the antibody or antigen-binding fragment thereof, as mentioned herein; and (ii) a second container for detection of the antibody or antigen-binding fragment thereof, wherein the second container comprises a label. The diagnostic kit of the present invention can further include at least one third container selected from the group consisting of a wash reagent and a detection reagent.

In one aspect, the present invention relates to a vaccine for immunizing an individual against a cancer disease associated with positive expression of PDEF. As used herein, a cancer disease associated with positive expression of PDEF includes, without limitation, breast cancer, prostate cancer, ovarian cancer, endometrial cancer, colon cancer, and cervical cancer. The vaccine includes a polypeptide corresponding to a PDEF fragment that is effective to induce an immune response to PDEF in the individual. Suitable PDEF fragments can include, for example, a PDEF fragment having (i) an amino acid sequence corresponding to SEQ ID NO:2, SEQ ID NO:3, and/or SEQ ID NO:4; (ii) an amino acid sequence having at least 8 continuous residues from SEQ ID NO:2, SEQ ID NO:3, or SEQ ID NO:4; or (iii) two or more amino acid sequences having at least 8 continuous residues from SEQ ID NO:2, SEQ ID NO:3, and/or SEQ ID NO:4. In addition to the PDEF fragment, the vaccine of the present invention can include a pharmacologically acceptable carrier or adjuvant.

In still another aspect, the present invention relates to a method for immunizing an individual against a cancer disease associated with positive PDEF expression. This method involves administering the vaccine of the present invention into the individual. Suitable individuals for PDEF immunization can include, without limitation, a individual that is high risk for, predisposed to, susceptible to, and/or diagnosed with said cancer disease associated with positive PDEF expression. The method is effective to immunize against such diseases that include, but are not limited to, breast cancer, prostate cancer, ovarian cancer, endometrial cancer, colon cancer, and/or cervical cancer.

In a further aspect, the present invention relates to a viral or plasmid expression vector. This viral or plasmid expression vector includes a nucleotide sequence that is operably linked to a promoter and that encodes an antigen. Suitable antigens can include, without limitation, a PDEF fragment having the following: (i) an amino acid sequence corresponding to SEQ ID NO:2, SEQ ID NO:3, and/or SEQ ID NO:4; (ii) an amino acid sequence having at least 8 continuous residues from SEQ ID NO:2, SEQ ID NO:3, or SEQ ID NO:4; or (iii) two or more amino acid sequences having at least 8 continuous residues from SEQ ID NO:2, SEQ ID NO:3, and/or SEQ ID NO:4.

The present invention also relates to a vaccine having (a) the expression vector of the present invention discussed herein and (b) a pharmaceutically acceptable carrier or adjuvant.

The present invention also relates to a method for immunizing an individual against a cancer disease associated with positive PDEF expression by administering this vaccine to the individual, where the individual is at high risk for, predisposed to, susceptible to, and/or diagnosed with said cancer disease associated with positive PDEF expression. The method is effective to immunize against such diseases that include, but are not limited to, breast cancer, prostate cancer, ovarian cancer, endometrial cancer, colon cancer, and/or cervical cancer.

In another aspect, the present invention relates to a method of preparing a polyclonal antibody that specifically binds with high affinity to PDEF. This methods involves immunizing an animal with a PDEF fragment having an amino acid sequence corresponding to SEQ ID NO:2, SEQ ID NO:3, and/or SEQ ID NO:4 under conditions effective to elicit an antibody response. The antibodies are isolated from the animal. Thereafter, this method involves screening the isolated antibodies using an immunohistochemical assay to identify a polyclonal antibody that specifically binds with high affinity to PDEF. The polyclonal antibody if then isolated. The present invention also relates to a polyclonal antibody produced by this method.

In still another aspect, this invention relates to a method for generating a monoclonal antibody that specifically binds with high affinity to PDEF. This method involves administering to an animal an amount of an immunogenic composition that includes a PDEF segment effective to stimulate a detectable immune response. A suitable PDEF segment can include, without limitation, an amino acid sequence corresponding SEQ ID NO:2, SEQ ID NO:3, and SEQ ID NO:4. Thereafter, antibody-producing cells are obtained from the animal and the antibody-producing cells are fused with myeloma cells to obtain antibody-producing hybridomas. A hybridoma is selected that produces a monoclonal antibody that specifically binds with high affinity to PDEF, where the high affinity is confirmed using an immunohistochemical assay. Thereafter, the selected hybridoma is cultured in a cell culture that produces the monoclonal antibody. The monoclonal antibody is then obtained from the cell culture.

The present invention also relates to a method of determining whether a human subject is susceptible to a type of cancer characterized by positive expression of PDEF. This method involves obtaining a tissue sample from a subject, where the tissue sample is suspected of being a cancer tumor tissue. The tissue sample is then contacted with the antibody or antigen-binding fragment thereof according to the present invention, and under conditions effective to allow for measuring the level of PDEF expression in the tissue sample. Under this method, measuring the level of PDEF expressed in the tissue sample using an immunohistochemical assay, whereby positive expression of PDEF indicates that the subject is susceptible to a type of cancer characterized by positive expression of PDEF.

In another aspect, the present invention relates to a method of prognostic stratification of a cancer patient for targeted therapeutic cancer treatment. This method involves obtaining a tissue sample from the cancer patient, where the tissue sample is suspected of including cancer tumor tissue. The tissue sample is contacted with the antibody or antigen-binding fragment thereof of the present invention so as to be effective to allow for measuring the level of PDEF expression in the tissue sample. The level of PDEF is then measured in the tissue sample using an immunohistochemical assay, whereby positive expression of PDEF indicates that the patient is in need of therapeutic treatment for a type of cancer characterized by positive expression of PDEF. Thereafter, the patient is provided with the therapeutic treatment effective for the type of cancer characterized by positive expression of PDEF. This method can be used to test tissue samples from breast tissue, prostate tissue, ovarian tissue, endometrial tissue, colon tissue, and cervical tissue, as they related to breast cancer, prostate cancer, ovarian cancer, endometrial cancer, colon cancer, and cervical cancer.

The present invention also relates to a method of treating or preventing a disease characterized by growth of tumor cells expressing PDEF. This method involves administering to a subject a vaccine according to the present invention, thereby inducing T cell immunity that inhibits growth of tumor cells that express PDEF.

In another embodiment, the present invention relates to another method of treating or preventing a disease characterized by growth of tumor cells expressing PDEF. The method involves administering to a subject a vaccine according to the present invention, thereby inducing T cell immunity that inhibits growth of tumor cells that express PDEF.

The present invention also relates to a method of treating or preventing a disease characterized by growth of tumor cells expressing PDEF, by administering to a subject a small molecule inhibitor that inhibits PDEF expression in tumors cell, thereby inhibiting growth of tumor cells that express PDEF. A suitable small molecule inhibitor can include, for example, an antisense oligonucleotide including at least 15 nucleotides and having a nucleotide sequence that is complementary to at least 15 nucleotides of an encoding nucleotide sequence of a PDEF fragment. The PDEF fragment encoded by the nucleotide sequence can encode an amino acid sequence selected from the group consisting of SEQ ID NO:2, SEQ ID NO:3, and SEQ ID NO:4; (ii) an amino acid sequence having at least 5 continuous residues from SEQ ID NO:2, SEQ ID NO:3, or SEQ ID NO:4; or (iii) two or more amino acid sequences having at least 5 continuous residues from SEQ ID NO:2, SEQ ID NO:3, and/or SEQ ID NO:4.

In one aspect, the present invention relates to a method for detecting pre-existing spontaneous T cell response to human PDEF in a serum sample of a subject. This method involves contacting the serum sample with peptides corresponding to SEQ ID NO:2, SEQ ID NO:3, and/or SEQ ID NO:4 under conditions such that an immunocomplex forms. The presence of the immunocomplex is then detected, where such detection indicates pre-existing spontaneous T cell response to human PDEF in a serum sample of the subject.

In another aspect, the present invention relates to a method for detecting pre-existing spontaneous antibody response to human PDEF in a sample of blood cells of a subject. This method involves contacting the sample of blood cells with overlapping peptides of at least 8 continuous residues of the amino acid sequences corresponding to SEQ ID NO:2, SEQ ID NO:3, and/or SEQ ID NO:4. T cell proliferation by enzyme-linked immunospot (ELIspot) assay is then measured, where positive detection indicates pre-existing spontaneous antibody response to human PDEF in a sample of blood cells of a subject.

The present invention also relates to a method for boosting immunity of a cancer patient to a cancer disease associated with positive expression of PDEF. This method involves obtaining a tissue sample from the cancer patient, where the tissue sample is suspected of including cancer tumor tissue. The tissue sample is contacted with the antibody or antigen-binding fragment thereof according to the present invention, under conditions effective to allow for measuring the level of PDEF expression in the tissue sample. The level of PDEF expressed in the tissue sample is measured using an immunohistochemical assay, whereby positive expression of PDEF indicates that the patient is in need of an additional immunization against PDEF. The patient is then tested for any pre-existing antibody or T cell response against PDEF, and finding of such response makes patient a better candidate for receiving vaccine treatment. The patient is then provided with a vaccine of the present invention under conditions effective to boost immunity of the cancer patient to the cancer disease associated with positive expression of PDEF. As contemplated by this method, the tissue sample can be selected from the following tissues, without limitation: breast tissue, ovarian tissue, endometrial tissue, colon tissue, and/or cervical tissue. Further, this method is effective in boosting the immunity of a cancer patient to one of the following cancer diseases associated with positive expression of PDEF: breast cancer, ovarian cancer, endometrial cancer, colon cancer, and/or cervical cancer.

The scientific literature supports the view that PDEF (Prostate derived Ets transcription factor) is a significant player in breast, prostate, and ovarian cancer progression (1, 2). However, as noted previously in the Background section, the lack of an anti-PDEF antibody that specifically binds to PDEF with high affinity has made it difficult to develop prognostic, diagnostic, and treatments for cancers associated with positive expression of PDEF. The present invention and the supporting Examples highlight the significance of an anti-PDEF antibody in assessing PDEF expression levels in tissue samples from cancer patients. Also, the importance and use of PDEF as a novel diagnostic/prognostic marker and a therapeutic target against breast, prostate, and ovarian cancers is contemplated by the present invention.

Together, these results demonstrate an important role for PDEF in breast and prostate cancer progression, and support PDEF as a novel prognostic marker in these cancers, as well as a target for developing specific therapies against these cancers. In ovarian cancer, PDEF expression associates with the cancer phenotype, suggesting a diagnostic application for PDEF in this cancer. Based on these observations, it is expected that, in the future, all newly diagnosed breast, prostate, and ovarian tumors will be analyzed for PDEF expression, in order to predict survival and to select patients for receiving additional treatments including novel therapies targeted to PDEF.

The anti-PDEF antibody of the present invention represents the first reagent useful for the evaluation of PDEF protein expression by immunohistochemistry in primary tumors from patients. The present invention also contemplates the use of monoclonal antibodies against the PDEF-1-104 segment and/or against specific peptides derived from this segment, or from other segments of PDEF, including PDEF-105-141 and PDEF-214-247, that show homology only to PDEF. Additionally, polyclonal or monoclonal antibodies against these PDEF peptides may be raised in various species of mammals in addition to rabbit, e.g., in mice or goat.

The anti-PDEF antibody (or antigen-binding fragment thereof) can be used to assay for PDEF expression levels in a number of prognostic and diagnostic methods. For example, the antibody of the present invention can be used for prognostic stratification of breast cancer patients to identify those at risk of early death.

The present invention further provides for the use of PDEF expression levels for prognostic stratification of patients, in particular, those with luminal breast tumors that comprise more than 80% of the newly diagnosed breast cancers. The latter include ER+ tumors, Her2/neu+ tumors, and apocrine breast tumors.

The present invention also provides for the use of PDEF expression levels to stratify luminal breast cancer patients with regard to the therapeutic course of action, i.e., patients with high PDEF expression may be eligible to receive additional treatments, including those targeted to PDEF itself.

The present invention provides for prognostic stratification of patients with prostate cancer based on the levels of PDEF expression in primary prostate tumors, with regard to risk of early cancer recurrence.

The present invention also provides for the use of PDEF expression levels to stratify prostate cancer patients with regard to the therapeutic course of action, i.e., patients with high PDEF expression may be eligible to receive additional treatments including those targeted to PDEF itself.

The present invention further provides for the use of PDEF antibody to diagnose ovarian cancer.

The present invention provides for prognostic stratification of patients with ovarian cancer based on the levels of PDEF expression in primary ovarian tumors, with regard to risk of early cancer recurrence or poor survival.

The present invention also provides for the use of PDEF expression levels to stratify ovarian cancer patients with regard to the therapeutic course of action, i.e., patients with high PDEF expression may be eligible to receive additional treatments including those targeted to PDEF itself.

The present invention further provides for use of PDEF antibody in other diseases in which changes in PDEF expression levels may dispose to disease development The present invention provides for use of the PDEF-1-104 peptide for developing novel therapeutics against breast, prostate, and ovarian cancers, including small molecule inhibitors against this segment of PDEF and vaccines derived from this segment of PDEF.

Additionally, the present invention provides for the use of PDEF-105-141 peptide for developing novel therapeutic against breast, prostate, and ovarian cancers, including small molecule inhibitors against this segment of PDEF and vaccines derived from this segment of PDEF.

The present invention further provides for the use of PDEF-214-247 peptide for developing novel therapeutic against breast, prostate, and ovarian cancers, including small molecule inhibitors against this segment of PDEF and vaccines derived from this segment of PDEF.

The present invention further provides for the use of PDEF-1-104, PDEF-105-141, and PDEF-214-247 peptides as probes to assess any pre-existing PDEF specific spontaneous immunity in breast and ovarian cancer patients. This would allow selection of patients to receive PDEF-based vaccines to boost their immunity with a view to induce strong immunity against breast and ovarian cancers.

The present invention is useful in overcoming the deficiencies in the prior art.

BRIEF DESCRIPTION OF DRAWINGS

FIG. 1 illustrates a blast homology alignment search for human sequences that show significant homology to various segments of PDEF. These include: (i) N-terminal PDEF unique segment spanning amino acid residues 1-104 (FIG. 1A); (ii) segment spanning amino acid residues 142-213 corresponding to the Pointed domain (FIG. 1B); (iii) segment spanning amino acid residues 248-331 defining the DNA binding Ets domain (FIG. 1C); (iv) PDEF unique segment spanning amino acid residues 105-141 (FIG. 1D) and v) PDEF unique segment spanning amino acid residues 214-247 (FIG. 1E).

FIG. 4B summarizes the lack of reactivity of PDEF antibody in other normal tissues. This reactivity pattern was similar to that previously reported for PDEF mRNA expression in normal human tissues (3), and further validates the specificity of this antibody.

DETAILED DESCRIPTION OF THE INVENTION

Various abbreviations and terms are used throughout to describe various aspects of the present invention. Below is a selected listing of certain of these abbreviations and terms.

As used herein, the abbreviation "PDEF" corresponds to Prostate derived Ets factor.

As used herein, the abbreviation "SPDEF" corresponds to Sam pointed domain containing Ets factor.

As used herein, the abbreviation "ER" corresponds to Estrogen receptor.

As used herein, the abbreviation "Her2/neu" corresponds to human epidermal growth factor receptor 2.

As used herein, the abbreviation "Ets" corresponds to erythrocyte transforming sequence, also known as E twenty-six (Ets) virus transforming sequence. This structural domain is present in 27 human proteins belonging to the Ets family to which PDEF also belongs. The Ets domain is used by these transcription factors to bind to DNA and regulate gene expression.

As used herein, the term "Pointed" corresponds to a structural motif present in proteins, primarily used in protein-protein interaction, in particular, in homo or hetero di- and oligomerization.

As used herein, the abbreviation "MCF-7" corresponds to a human breast tumor cell line.

As used herein, the abbreviation "MCF-12A" corresponds to a low malignancy epithelial cell line derived from normal human breast.

As used herein, the abbreviation "s.c." corresponds to Sub cutaneous.

As used herein, the abbreviation "pET 15b" corresponds to a plasmid expression vector for production of recombinant proteins in bacteria.

As used herein, the abbreviation "IPTG" corresponds to isopropyl β-D-1-thiogalactopyranoside.

As used herein, the abbreviation "PSA" corresponds to prostate specific antigen.

As used herein, the term "PDEF-1-104" corresponds to an N-terminal segment of PDEF protein that includes amino acid residuesI to 104 of PDEF.

As used herein, the term "Gleason score" corresponds to a score given to prostate cancer based upon its microscopic appearance. Cancers with a higher Gleason score are more aggressive and have a worse prognosis.

As used herein, the term "Biochemical PSA failure" refers to a surrogate endpoint for cancer recurrence and is defined as three consecutive rises of the PSA, before a failure is declared.

As used herein, the abbreviation "Pse-DC" corresponds to dendritic cells transfected with Pse expression plasmid.

As used herein, the abbreviation term "Vector-DC" corresponds to dendritic cells transfected with vector plasmid.

As used herein, the abbreviation "Her2/neu-DC" corresponds to dendritic cells transfected with Her2/neu expression plasmid.

As used herein, the abbreviation "IFN-γ" corresponds to interferon-gamma.

As used herein, the abbreviation "IL-2" corresponds to interleukin-2.

Figure 2:
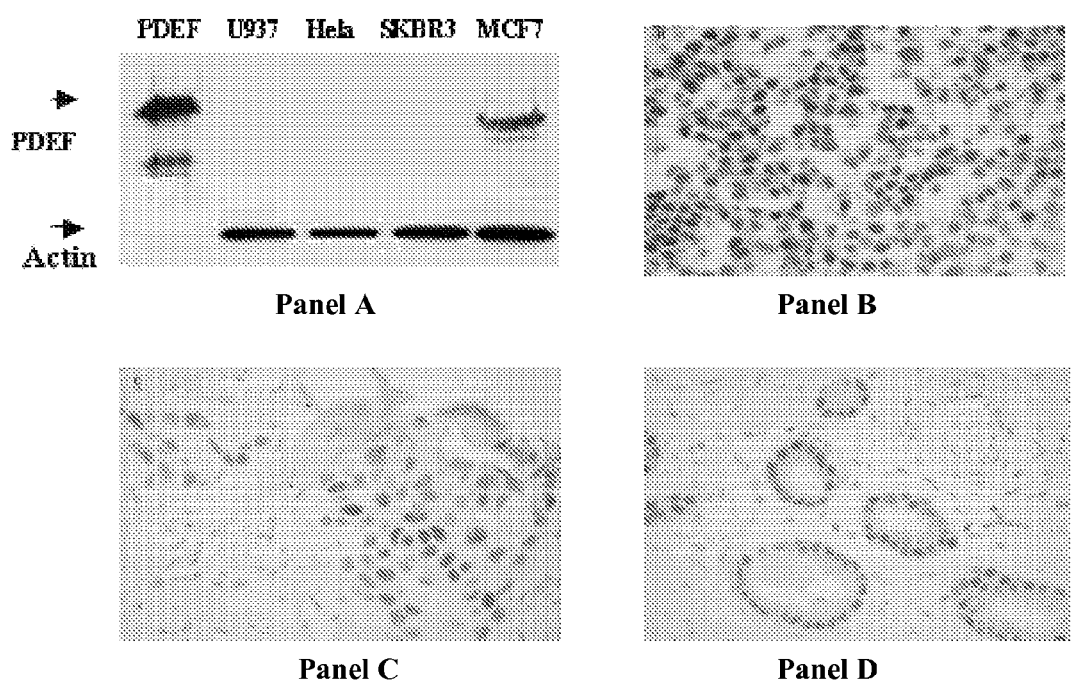
FIG. 2 illustrates testing for the specificity of anti-PDEF antibodies by Western blotting and immunohistochemistry. Panel A shows analysis of PDEF protein expression in breast and non-breast tumor cell lines by Western blotting. Equal amounts of total protein from breast tumor cell lines MCF-7, SKBR3 and from non-breast tumor cell lines Hela and U937 were run on 12% SDS PAGE and transferred to nitrocellulose membrane. The upper-half of this panel shows the result of probing the blot with anti-PDEF antibodies and the lower-half shows a similar blot following probing with anti-actin antibody. The Panels B, C and D respectively show specific nuclear staining of PDEF protein in the epithelial tumor cells from MCF-7 breast tumor cell line and in tissue section from a primary breast carcinoma and a primary prostate carcinoma.

The present invention relates to anti-PDEF antibodies that specifically bind with high affinity to human PDEF. The anti-PDEF antibodies of the present invention have been confirmed to have high affinity to human PDEF using immunohistochemical assays. The antibodies of the present invention have been shown to react with a protein that migrates at about 46 kD in size, which is similar to the migration of recombinant PDEF protein and of PDEF protein expressed by an MCF-12A cell line that was transfected with PDEF expression plasmid (FIG. 2). Due to their high affinity and their ability to be detected in immunohistochemical assays, the anti-PDEF antibodies of the present invention can be used, inter alia, to evaluate PDEF expression by immunohistochemistry in the primary tumor samples from patients. The functionality of the anti-PDEF antibodies of the present invention makes these antibodies useful in numerous prognostic and diagnostic applications. Further, the anti-PDEF antibodies of the present invention can be used to assist in developing vaccines and other treatments of cancers that are associated with positive expression of PDEF.

The uniqueness of the anti-PDEF antibodies of the present invention as compared with previously reported anti-PDEF antibodies is readily apparent, as noted below.

For example, as mentioned in the Background section hereof, antibodies against specific peptides from PDEF are available from commercial sources. However, their use to evaluate PDEF expression by immunohistochemistry in the primary tumor samples from patients has not been demonstrated. Notably, a PDEF antibody (termed PDEF (N-14): sc-46446), apparently raised against an N-terminal peptide, has been described. (See Goat Anti-PDEF, N-14 polyclonal antibody, available from Santa Cruz Biotechnology, Inc.). In Western blot assays, this antibody reacts with a protein that migrates at 37 to 38 kD size. (See www.scbt.com/datasheet-46446-pdef-n-14-antibody.html). However, this is inconsistent with the migration patterns of recombinant PDEF protein and of PDEF protein expressed by MCF-12A cell line that was transfected with PDEF expression plasmid, both of which migrate at about 46 kD size. The N-14 antibody is, therefore, different from the antibodies of the present invention. Additionally, the data specification sheet for the N-14 antibody states that it is not recommended for use in clinical diagnosis, which is in stark contrast to the anti-PDEF antibodies, which are ideal for immunohistochemical assay based diagnostics.

Recently, another antibody to a large PDEF segment comprising amino acid residues 1-250 was described. However, since this 1-250 residue segment contains the Pointed domain that is present in many other human Ets proteins (see FIG. 1B), use of this antibody is also likely to yield non-specific reactivity with other proteins in addition to PDEF. Consequently, its specificity for PDEF in immunohistochemical assay for staining PDEF in tissue sections from a patient's tumors remains to be demonstrated. A possible explanation for non-specific reactivity of anti-PDEF antibodies in immunohistochemistry assays may be that during antigen retrieval process, protein renaturation takes place, and this may allow generation of new epitopes that are not present under the denaturing conditions of Western blotting. This deficiency is not a problem with the anti-PDEF antibodies of the present invention.

The uniqueness of the anti-PDEF antibodies of the present invention can also be demonstrated by comparing it to another antibody purported to be raised against the 1-104 residues of PDEF. This particular polyclonal antibody was described by Ghadersohi et al. (6, 7). Unlike the anti-PDEF antibodies of the present invention, the specificity of the antibody of Ghadersohi et al. to PDEF was not demonstrated in an immunohistochemical assay. In particular, Ghadersohi et al. were not able to use their antibody to demonstrate correspondence between PDEF mRNA and protein expression in a panel of normal human tissues. Ghadersohi et al. were further unable to use their antibody to demonstrate increase in expression of PDEF protein in the breast tumor tissue in comparison to adjacent benign breast tissue in matched samples from patients. To the contrary, the antibody of Ghadersohi et al. showed strong reactivity with normal breast and ovarian tissues (6, 7), and weak reactivity with tumors from these tissues.

The results with regard to the polyclonal antibody reported by Ghadersohi et al. are contrary to the results obtained by the inventor with regard to PDEF expression in breast and ovarian tissue (1, 2). Further, the anti-PDEF antibodies of the present invention have been validated with regard to their specificity using a number of experiments shown in FIGS. 2-5. By contrast, the antibody purportedly generated by Ghadersohi et al. against residues 1-104 of PDEF does not appear to show specificity for PDEF in the immunohistochemistry assay. Therefore, there is compelling evidence to show that the anti-PDEF antibodies of the present invention are, indeed, distinguishable from any other purported anti-PDEF antibody described in the art.

In one embodiment, the human PDEF that was used to generate the specifically binding and high affinity anti-PDEF antibodies corresponded to the polypeptide product of a *Homo sapiens* SAM pointed domain-containing ets transcription factor (referred to herein as "SPDEF") having NCBI Accession No. NM_012391 (incorporated by reference herein in its entirety). In particular, this PDEF has an amino acid sequence of SEQ ID NO:1 is as follows:

```
                                              (SEQ ID NO: 1)
MGSASPGLSSVSPSHLLLPPDTVSRTGLEKAAAGAVGLERRDWSPSPPAT

PEQGLSAFYLSYFDMLYPEDSSWAAKAPGASSREEPPEEPEQCPVIDSQA

PAGSLDLVPGGLTLEEHSLEQVQSMVVGEVLKDIETACKLLNITADPMDW

SPSNVQKWLLWTEHQYRLPPMGKAFQELAGKELCAMSEEQFRQRSPLGGD

VLHAHLDIWKSAAWMKERTSPGAIHYCASTSEESWTDSEVDSSCSGQPIH

LWQFLKELLLKPHSYGRFIRWLNKEKGIFKIEDSAQVARLWGIRKNRPAM

NYDKLSRSIRQYYKKGIIRKPDISQRLVYQFVHPI
```

The anti-PDEF antibody or antigen-binding fragment thereof of the present invention can be raised against a segment of the PDEF of SEQ ID NO:1 that is unique to PDEF, in that it does not have high homology with other non-PDEF Ets family members or any other polypeptides.

As provided herein, the present invention relates to various embodiments of anti-PDEF antibodies (or antigen-binding fragments thereof) that are raised against the following amino acid segments of the PDEF of SEQ ID NO:1: (i) residues 1-104 of SEQ ID NO:1; (ii) residues 105-141 of SEQ ID NO:1; and/or (iii) residues 214-247 of SEQ ID NO:1.

Amino acid residues 1-104 of the human PDEF of SEQ ID NO:1 are described below and correspond to SEQ ID NO:2, as follows:

```
                                              (SEQ ID NO: 2)
MGSASPGLSSVSPSHLLLPPDTVSRTGLEKAAAGAVGLERRDWSPSPPAT

PEQGLSAFYLSYFDMLYPEDSSWAAKAPGASSREEPPEEPEQCPVIDSQA

PAGS
```

Amino acid residues 105-141 of the human PDEF of SEQ ID NO:1 are described below and correspond to SEQ ID NO:3, as follows:

```
                                              (SEQ ID NO: 3)
LDLVPGGLTLEEHSLEQVQSMVVGEVLKDIETACKLL
```

Amino acid residues 214-247 of the human PDEF of SEQ ID NO:1 are described below and correspond to SEQ ID NO:4, as follows:

```
                                              (SEQ ID NO: 4)
SAAWMKERTSPGAIHYCASTSEESWTDSEVDSSCSGQ
```

In one aspect, the present invention relates to an isolated antibody or antigen-binding fragment thereof that specifically binds with high affinity to at least a portion of a segment of a human PDEF. Suitable segments of PDEF can include, but are not limited to, the following: (a) amino acid residues 1-104 of SEQ ID NO:1; (b) amino acid residues 105-141 of SEQ ID NO:1; (c) amino acid residues 214-247 of SEQ ID NO:1; or (d) the like.

In one embodiment, the antigen-binding fragment can include, for example, an F(ab')$_2$ fragment, an Fab' fragment, an Fab fragment, or an Fv fragment.

The antibody or antigen-binding fragment thereof of the present invention can be in the form of a polyclonal antibody, a monoclonal antibody, and/or a single chain antibody.

Monoclonal antibody production may be effected by techniques which are well-known in the art. Basically, the process involves first obtaining immune cells (lymphocytes) from the spleen of a mammal (e.g., mouse), which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature*, 256:495 (1975), which is hereby incorporated by reference in its entirety.

As an example, mammalian lymphocytes are immunized by in vivo immunization of the animal (e.g., a mouse) with the PDEF peptide fragment in accordance with the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents. (See Milstein and Kohler, *Eur. J. Immunol.*, 6:511 (1976), which is hereby incorporated by reference in its entirety). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described. However, for the purpose of the present invention, it is important that the monoclonal antibodies specifically bind with high affinity to PDEF so that they can be used in immunohistochemistry assays according to the present invention.

Procedures for raising polyclonal antibodies are also well known. Typically, such antibodies can be raised by administering the subject protein or polypeptide (e.g., the PDEF fragments according to the present invention) subcutaneously to New Zealand white rabbits which have first been bled to obtain pre-immune serum. The antigens can be injected at a total volume of 100 μl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized (e.g., pentobarbital 150 mg/Kg IV). This and other procedures for raising polyclonal antibodies are disclosed in E. Harlow, et. al., editors, *Antibodies: A Laboratory Manual* (1988), which is hereby incorporated by reference in its entirety. However, for the purpose of the present invention, it is important that the polyclonal antibodies specifically bind with high affinity to PDEF so that they can be used in immunohistochemistry assays according to the present invention.

Polyclonal sera rendered monospecific for a particular target PDEF segment may be made, for example, by preparing a PDEF polyclonal antiserum using the procedures described above, and then exposing the polyclonal antiserum to hydroxyapatite beads coated with a non-target peptide fragment or non-target PDEF fragment, thereby removing antibodies cross-reactive to non-target peptide fragment or non-target PDEF fragment. Monospecificity for a particular PDEF fragment can be determined by ELISA assay. Absorbance analyses can then be performed to determine monospecificity for the target PDEF fragment. Sera demonstrated to be monospecific can be employed in the assays of the present invention, as one embodiment.

As indicated above, biological agents suitable for use in accordance with the present invention include antibodies, such as monoclonal or polyclonal antibodies. In addition, antibody fragments (antigen binding portions), half-antibodies, hybrid derivatives, probes, and other molecular constructs that are specific for a particular PDEF fragment may also be utilized.

As mentioned previously, exemplary antibody fragments include, without limitation, Fab fragments, Fab' fragments, F(ab)$_2$ fragments, F(ab')$_2$ fragments, Fd fragments, Fv fragments, dAb fragments, and isolated complementarity determining regions ("CDRs") (see U.S. Pat. Nos. 7,037,498, 7,034,121, 7,041,870, and 7,074,405, which are hereby incorporated by reference in their entirety). These antibody fragments can be made by conventional procedures, such as proteolytic fragmentation procedures, as described in J. Goding, *Monoclonal Antibodies: Principles and Practice*, pp. 98-118 (N.Y. Academic Press 1983), which is hereby incorporated by reference in its entirety.

In addition, the antibody or antigen-binding fragment thereof can be detectably labeled. Suitable detectable labels for use with the antibody (or antigen-binding fragment thereof) of the present invention can include, without limitation, a radioisotope, an affinity label, an enzymatic label, a fluorescent label, and a paramagnetic atom.

As indicated above, detection of PDEF may also be accomplished using any of a variety of other immunoassays in conjunction with the anti-PDEF antibodies of the present invention. For example, by radioactively labeling the antibody or antibody fragment or probe of the present invention, it is possible to detect the PDEF protein that the antibody or antibody fragment or probe was designed for through the use of a radioimmunoassay (RIA) (see, e.g., Weintraub, *Principles of Radioimmunoassays, Seventh Training Course on Radioligand Assay Techniques*, The Endocrine Society (1986), which is hereby incorporated by reference in its entirety). The radioactive isotope can be detected by such means as the use of a gamma counter or a scintillation counter or by autoradiography.

It is also possible to label the antibody or antibody fragment or probe of the present invention with a fluorescent compound. When the fluorescently labeled antibody or antibody fragment or probe is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine, but others known in the art are contemplated by the present invention.

The antibody or antibody fragment or probe of the present invention can also be detectably labeled using fluorescence emitting metals such as $^{152}$Eu, or others of the lanthanide series. These metals can be attached to the antibody or antibody fragment or probe of the present invention using such metal chelating groups as diethylenetriaminepentacetic acid (DTPA) or ethylenediaminetetraacetic acid (EDTA).

The antibody or antibody fragment or probe of the present invention can also be detectably labeled by coupling it to a chemiluminescent compound. The presence of the chemiluminescent-tagged antibody or antibody fragment or probe is then determined by detecting the presence of luminescence that arises during the course of a chemical reaction. Examples of particularly useful chemiluminescent labeling compounds are luminol, isoluminol, theromatic acridinium ester, imidazole, acridinium salt, and oxalate ester.

Likewise, a bioluminescent compound may be used to label the antibody or antibody fragment or probe of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In order to validate the specificity and binding affinity of any antibodies or antigen-binding fragments thereof to PDEF, it is important to conduct immunohistochemical assays using the antibodies (antigen-binding fragments). As noted previously, unlike previously reported anti-PDEF antibodies in the art, the antibody or antigen-binding fragment thereof of the present invention has been shown to bind specifically and with high affinity to PDEF using immunohistochemical assays. Therefore, a suitable antibody or antigen-binding fragment thereof of the present invention is one that is characterized as exhibiting: (a) strong staining intensity as determined in an immunohistochemical assay with three or less of the normal tissues being selected from the group consisting of prostate gland tissue, salivary gland tissue, and trachea/bronchus tissue; and (b) negative staining intensity as determined by an immunohistochemical assay with three or more tissues selected from the group consisting of adrenal gland tissue, blood, brain tissue, bone marrow, heart tissue, liver tissue, lung tissue, lymph node tissue, kidney tissue, ovary tissue, placenta tissue, spleen tissue, skeletal muscle tissue, thymus tissue, and testis tissue.

In accordance with the present invention, particularly regarding the immunohistochemical assay aspect thereof, PDEF-negative tissue or samples can include, without limitation, adrenal gland tissue, blood, brain tissue, bone marrow tissue, heart tissue, liver tissue, lung tissue, lymph node tissue, kidney tissue, ovary tissue, placenta tissue, spleen tissue, skeletal muscle tissue, thymus tissue, and testis tissue.

In accordance with the present invention, particularly regarding the immunohistochemical assay aspect thereof, criteria for positive expression for PDEF can include, without limitation: (i) a minimum of 30% tumor cells staining at 1+ intensity; (ii) a minimum of 15% tumor cells staining at 2+ intensity; or (iii) a minimum of 10% tumor cells staining at 3+ intensity. Similar criteria can also be applied for normal tissues. Criteria for "negative" expression for PDEF can include, without limitation, any tissue that contains less than 5% cells staining positive for PDEF. "Strong" expression is defined herein as a minimum of 30% of cells stained at 3+ intensity.

To generate more specific PDEF antibodies, a comparison of the sequence of PDEF with other members of the Ets factor family was conducted, which showed that a large segment at the N-terminus of the PDEF protein, spanning amino acid residues 1-140 (PDEF-1-140), showed homology only to PDEF, and not to any other human protein. This PDEF segment was therefore produced as recombinant protein in bacteria and then used to immunize rabbits to produce polyclonal antibodies, as discussed in more detail in the Examples.

As with previously described antibodies to full-length PDEF, the antibodies to PDEF-1-104 peptide reacted specifically with PDEF protein by Western blot assay. However, since application of an antibody in clinical diagnosis requires the use of immunohistochemistry assay, it was necessary to demonstrate the specificity of the antibody in the immunohistochemistry assay. For this purpose, an assay was developed that included testing the reactivity of the antibody of the present invention in a panel of normal human tissues (A6). These included: (i) normal prostate and trachea/bronchus tissues that were previously shown to express PDEF and (ii) a number of other normal tissues such as brain, heart, kidney, liver, lung, skeletal muscle, spleen, testis that did not express PDEF mRNA (A1-3). When this assay was done, the PDEF-1-104 antibody showed a reactivity pattern similar to that described for PDEF mRNA expression, and this validated the specificity of the PDEF-1-104 antibody for PDEF in the immunohistochemical assay, to evaluate PDEF expression in a patient's samples.

Previous work had shown frequent over expression of PDEF mRNA in human breast and ovarian tumors (3, 21); however, due to lack of suitable antibodies, PDEF protein expression could not be evaluated. Consequently, a direct role for PDEF in tumor progression could not be proposed or ascertained. Meanwhile, other labs using a small number of patient samples reported the loss of PDEF protein expression in progression from benign breast and prostate tissues to carcinomas (4, 5), suggesting an apparent loss of PDEF protein in the tumor tissue. However, these studies used antibodies to full-length PDEF proteins that were demonstrated to give uncharacteristic reactivity with normal tissues, presumably due to cross reaction of those antibodies with the homologous Ets and Pointed domains present in other Ets proteins. This problem is particularly acute since many of the non-PDEF Ets factors are expressed at much higher levels than PDEF in the normal mammary gland and in mammary tumor tissues (22, 23).

In contrast, the present invention relates to a well-characterized antibody that was used to analyze a large number of patients' samples. Therefore, the anti-PDEF antibody of the present invention was used to demonstrate the first showing of over expression of the PDEF protein in progression from benign breast, prostate, and ovarian tissues to carcinomas, supporting an important role for PDEF in the progression of these cancers.

In a particular embodiment, the isolated antibody or antigen-binding fragment thereof of the present invention is an anti-PDEF polyclonal antibody that is effective for use in prognosis and diagnosis of PDEF in tissue, blood, or other samples. The specificity and high affinity of this anti-PDEF antibody to PDEF has been validated using immunohistochemical assays, as further described in the Examples described herein. This isolated anti-PDEF antibody has been deposited for storage and dissemination at the inventor's laboratory, located at the Department of Immunology, Roswell Park Cancer Institute, Elm and Carlton Streets, Buffalo, N.Y. 14263.

In another aspect, the present invention relates to a hybridoma that produces the antibody according to the present invention, particularly an antibody of the present invention where the antibody is a monoclonal antibody.

In yet another aspect, the present invention relates to a diagnostic kit. This kit can include, without limitation, (a) a first container containing the antibody or antigen-binding fragment thereof, as mentioned herein; and (b) a second container for detection of the antibody or antigen-binding fragment thereof, wherein the second container comprises a label. The diagnostic kit of the present invention can further include at least one third container selected from the group consisting of a wash reagent and a detection reagent.

Because the present invention provides, for the first time, an anti-PDEF antibody that specifically binds to PDEF with high affinity, and because of the importance of PDEF in the progression of certain types of cancer, the present invention now makes it possible to use PDEF as a biomarker for prognostic and diagnostic methods for such cancers. The use of PDEF as a biomarker for certain of these particular cancers is described below.

It should be pointed out that evaluating the expression of a putative cancer biomarker by immunohistochemistry is critical since this method is primarily used in clinical diagnosis. Specifically, immunohistochemistry provides a much more detailed picture of the characteristic of a biomarker expression in the tumor and its microenvironment, i.e., (i) whether the expression is restricted to epithelial tumor cells; (ii) whether increased expression is due to increased number of tumor cells or due to high level staining by a small fraction of cells; and or both; and (iii) whether other cells in the tumor microenvironment including inflammatory leukocytes, endothelial cells, and/or stromal cells express the specific biomarker.

In contrast, methods such as Western blotting do not provide such detail. Consequently, immunohistochemistry is the primary assay used for evaluating the expression of prognostic, predictive, and therapeutic tumor markers. Unlike other apparent anti-PDEF antibodies described in the art, the anti-PDEF antibody of the present invention has been shown to be effective in immunohistochemistry assays.

As examples of immunohistochemistry assays used in tandem with other biomarkers in the art (i.e., other than the PDEF biomarker), expression of the ER and Her2/neu in breast cancer and of androgen receptor (AR) in prostate cancer is primarily done by immunohistochemistry assays. Therefore, it becomes necessary to demonstrate the specificity of an antibody to novel cancer biomarkers in an immunohistochemical assay.

As indicated previously, despite recent gains, primarily stemming from the use of mammography for early detection of breast cancer and the PSA test for prostate cancer, mortality rates from advanced stage and metastatic disease remain unchanged. Novel biomarkers of clinical significance are needed to more accurately predict the course of the disease and to serve as targets for developing novel therapeutics to minimize mortality from breast, prostate and ovarian cancers.

For example, estrogen receptor and Her2/neu are the two currently known biomarkers of clinical significance that predict the course of disease and serve as targets against which specific inhibitors and/or antibodies have shown considerable clinical benefits to breast cancer patients. However, many patients develop resistance to these single agent-targeted treatment approaches and continue to suffer from disease recurrence and progression. Novel biomarkers of clinical significance are needed to minimize disease recurrence and progression in breast cancer patients. To that end, PDEF appears to be a highly promising novel prognostic/predictive marker and a target against breast cancer. Moreover, it is frequently expressed in ER+, Her2/neu-positive, and apocrine breast tumors of luminal origin (FIG. 11) that, together, comprise more than 80% of the newly diagnosed breast cancers. Simultaneous targeting of ER or Her2/neu with PDEF could provide an important novel approach to control of disease progression in a large population of breast cancer patients.

In prostate cancer, periodic monitoring of PSA levels is used to follow disease recurrence; and three consecutive increases in PSA levels is a surrogate marker of disease recurrence. However, in many cases, this is too late to offer effective additional treatments to patients, so the ability to predict the risk of disease recurrence early is important to have a better chance at effective treatments. To that end, high PDEF expression levels in primary tumors should allow early identification of the patients at high risk for cancer recurrence and those patients could receive additional treatments including those targeted to PDEF itself. Another study previously suggested a role for PDEF in prostate cancer progression based on the ability of PDEF to induce PSA expression in a prostate tumor cell line (19). Since then, those same authors have published work that contradicts their earlier proposal (20). Investigations regarding the present invention represent the first report to provide direct evidence for a role for PDEF in prostate tumor progression, based on the correlation with higher Gleason score and early Biochemical PSA failure. Again, this was possible because of the high specificity of the anti-PDEF antibody of the present invention to PDEF and the usefulness and effectiveness of this antibody in an immunohistochemistry assay.

In ovarian cancer, PDEF is not expressed in normal ovaries or in benign cystadenomas that are considered as precursors to cancer. Consequently, PDEF may serve as a diagnostic marker of cancer in ovarian cancer. Further, since PDEF is a transcription factor, some of the downstream target genes induced by PDEF could encode secreted or shed proteins that may appear in the serum, and serve as markers for early detection of ovarian cancer. Additionally, like breast and prostate cancer, PDEF could serve as a target for developing novel therapies against ovarian cancer.

It should be noted that two other studies, using PDEF mRNA quantitation, did not reveal any significant differences in the survival of patients (16) or revealed a correlation between lack of PDEF expression and poor survival of breast cancer patients (6). However, in these studies, basal subtype of breast tumors that are quite aggressive, constitute about 15% of breast tumors and naturally lack PDEF expression were not excluded from analyses. This could have masked the effect of high PDEF expression in luminal breast tumors present in the analysis cohorts. The basal subtype of breast tumors are a biologically distinct entity carrying a unique gene expression signature that is different from other breast cancer subtypes including ER+, Her2/neu+ and AR+breast cancer subtypes, each with distinct propensity for progression (17). Therefore, it is critical to evaluate the prognostic utility of a given biomarkers within the same breast cancer subtype.

Figure 10:
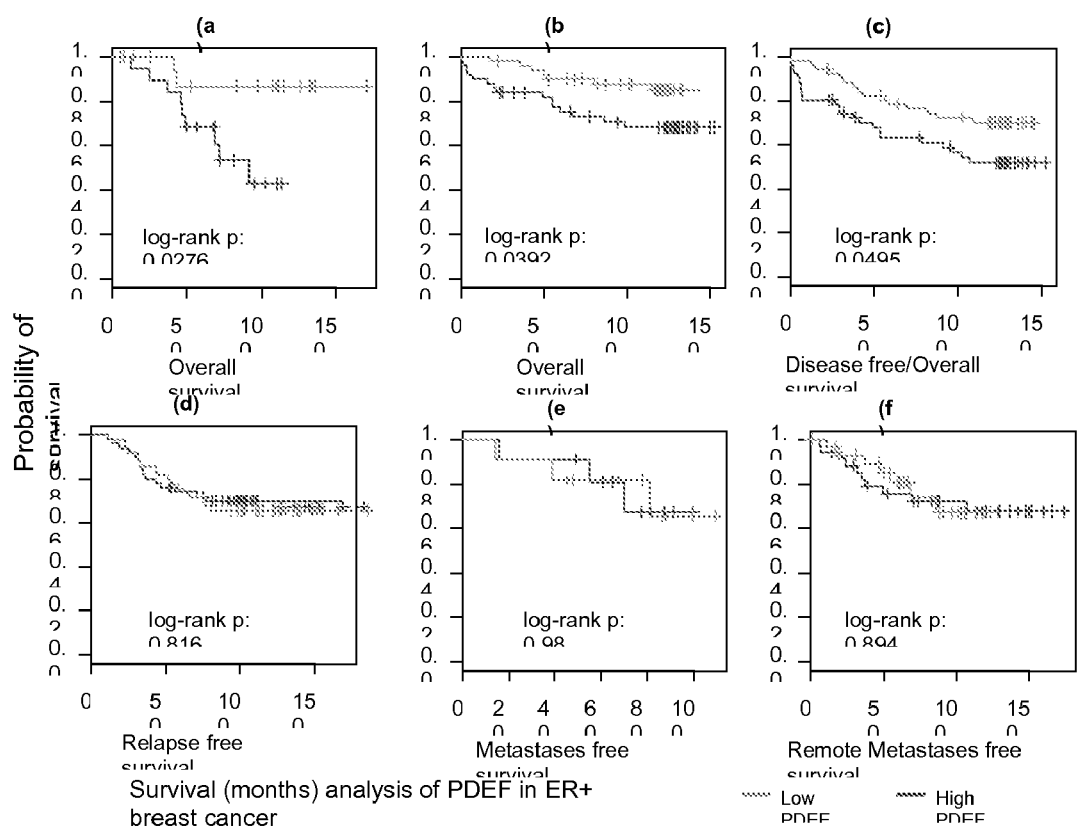
FIG. 10 illustrates a survival analysis with PDEF expression in patients with ER-positive breast cancer. Six datasets with patient survival data and PDEF expression data were studied. For each dataset, the low 25% quartile of PDEF expressing samples was categorized as low-expression samples; and the high 25% quartile as high-expression samples. Comparison of these low and high expression cohorts from the datasets (a) Chin et al. (9) and (b) Miller et al. (10) showed significantly poor overall survival for the PDEF high expression cohort. Also, in the dataset (c) of Ivshina et al (11) that includes mixed clinical outcome data on overall survival and metastases-free survival, a significant difference was observed between low and high PDEF expression cohorts. The log-rank test p-values are also shown in the figure. In contrast, no significant difference was observed between low and high PDEF expression cohorts with respect to relapse-free or metastases-free survival of patients in the datasets of (d) Wang et al. (12); (e) Minn et al. (13), and (f) Sotirious et al. (14).

Accordingly, in the analysis relating to the present invention shown in FIG. 10, only ER+ luminal subtype breast tumors that constitute about ⅔ rd of newly diagnosed breast cancer were analyzed, and as shown, in three independent datasets high PDEF levels in tumors showed significant correlation with poor overall survival of patients. Data in FIG. 10 showed no correlation between high PDEF expression and tumor relapse and metastases. Presumably, PDEF as a transcription factor alters the expression of genes to enhance anchorage independent tumor cell survival and decrease tumor cell apoptosis (18) and not genes that promote tumor recurrence, invasion and metastasis.

As noted, another novel finding due to the present invention is the correlation of high PDEF expression with poor overall survival of breast cancer patients, in particular, for luminal lineage derived tumors, as demonstrated for the ER+ breast tumors in FIG. 10. This correlation does not apply to tumors arising from the basal cell lineage that comprise about 15% of the newly diagnosed breast cancer. These tumors inherently do not express PDEF and their aggressive behavior may be attributable to their mesenchymal like phenotype, which renders tumors more motile and invasive.

Due to its specificity to PDEF and its applicability to immunohistochemical assays, the anti-PDEF antibody of the present invention can be used in detecting the PDEF biomarker with regard to all of the cancers described above, as well as any other cancers associated with positive expression of PDEF.

In accordance with the present invention, vaccines can be derived from the PDEF-unique peptides of SEQ ID NO:2, SEQ ID NO:3; and SEQ ID NO:4. For example, suitable types of vaccines can include, without limitation, (i) DNA or RNA viral vectors incorporating the encoded peptide sequences; (ii) plasmid vectors using cytomegalo virus promoter and the encoded PDEF-unique peptides; (iii) plasmid vectors used in conjunction with electroporation to enhance their expression; (iv) overlapping peptides of 8 to 15 amino acids long as peptide vaccines in conjunction with an adjuvant; and (v) nanoparticles including 8-15 amino acid long peptides emulsified with an adjuvant.

Various pharmacologically acceptable carriers or adjuvants well known in the art can be used with the vaccines of the present invention.

In one aspect, the present invention relates to a vaccine for immunizing an individual against a cancer disease associated with positive expression of PDEF. As used herein, a cancer disease associated with positive expression of PDEF includes, without limitation, breast cancer, prostate cancer, ovarian cancer, endometrial cancer, colon cancer, and cervical cancer. The vaccine includes a polypeptide corresponding to a PDEF fragment that is effective to induce an immune response to PDEF in the individual. Suitable PDEF fragments can include, for example, a PDEF fragment having (i) an amino acid sequence corresponding to SEQ ID NO:2, SEQ ID NO:3, and/or SEQ ID NO:4; (ii) an amino acid sequence having at least 8 continuous residues from SEQ ID NO:2, SEQ ID NO:3, or SEQ ID NO:4; or (iii) two or more amino acid sequences having at least 8 continuous residues from SEQ ID NO:2, SEQ ID NO:3, and/or SEQ ID NO:4. In addition to the PDEF fragment, the vaccine of the present invention can included a pharmacologically acceptable carrier or adjuvant.

In one embodiment, the vaccine can further include a nanoparticle vaccine having a peptide of at least 8 continuous residues from SEQ ID NO:2, SEQ ID NO:3, and/or SEQ ID NO:4.

In still another aspect, the present invention relates to a method for immunizing an individual against a cancer disease associated with positive PDEF expression. This method involves administering the vaccine of the present invention into the individual. Suitable individuals for PDEF immunization can include, without limitation, a individual that is high risk for, predisposed to, susceptible to, and/or diagnosed with said cancer disease associated with positive PDEF expression. The method is effective to immunize against such diseases that include, but are not limited to, breast cancer, prostate cancer, ovarian cancer, endometrial cancer, colon cancer, and/or cervical cancer.

In a further aspect, the present invention relates to a viral or plasmid expression vector. This viral or plasmid expression vector includes a nucleotide sequence that is operably linked to a promoter and that encodes an antigen. Suitable antigens can include, without limitation, a PDEF fragment having the following: (i) an amino acid sequence corresponding to SEQ ID NO:2, SEQ ID NO:3, and/or SEQ ID NO:4; (ii) an amino acid sequence having at least 8 continuous residues from SEQ ID NO:2, SEQ ID NO:3, or SEQ ID NO:4; or (iii) two or more amino acid sequences having at least 8 continuous residues from SEQ ID NO:2, SEQ ID NO:3, and/or SEQ ID NO:4.

The present invention also relates to a vaccine having (a) the expression vector of the present invention discussed herein and (b) a pharmacologically acceptable carrier or adjuvant.

The present invention further relates to a method for immunizing an individual against a cancer disease associated with positive PDEF expression by administering the vaccine of the present invention to the individual, where the individual is at high risk for, predisposed to, susceptible to, and/or diagnosed with the cancer disease associated with positive PDEF expression. The method is effective to immunize against such diseases that include, but are not limited to, breast cancer, prostate cancer, ovarian cancer, endometrial cancer, colon cancer, and/or cervical cancer.

PDEF is over expressed early in in situ breast carcinomas. Therefore, PDEF-based therapeutics can also be applied to primary prevention of breast cancer. Prophylactic vaccination is of special interest to older women over age 65, since the incidence of breast cancer in this age group is more than 6-fold higher than in younger women, and about 50% of the newly diagnosed breast cancers occur in this age group. There are an estimated 29 million women over age 65 in the United States alone who are at high risk for developing breast cancer, and they would benefit from preventive approaches targeted to PDEF. This suggests the potential for high impact of the present invention on the primary prevention of breast cancer.

In another aspect, the present invention relates to a method of preparing a polyclonal antibody that specifically binds with high affinity to PDEF. This method involves immunizing an animal with a PDEF fragment having an amino acid sequence corresponding to SEQ ID NO:2, SEQ ID NO:3, and/or SEQ ID NO:4 under conditions effective to elicit an antibody response. The antibodies are isolated from the animal. Thereafter, this method involves screening the isolated antibodies using an immunohistochemical assay to identify a polyclonal antibody that specifically binds with high affinity to PDEF. The polyclonal antibody if then isolated. The present invention also relates to a polyclonal antibody produced by this method.

In still another aspect, this invention relates to a method for generating a monoclonal antibody that specifically binds with high affinity to PDEF. This method involves administering to an animal an amount of an immunogenic composition that includes a PDEF segment effective to stimulate a detectable immune response. A suitable PDEF segment can include, without limitation, an amino acid sequence corresponding SEQ ID NO:2, SEQ ID NO:3, and SEQ ID NO:4. Thereafter, antibody-producing cells are obtained from the animal and the antibody-producing cells are fused with myeloma cells to obtain antibody-producing hybridomas. A hybridoma is selected that produces a monoclonal antibody that specifically binds with high affinity to PDEF, where the high affinity is confirmed using an immunohistochemical assay. Thereafter, the selected hybridoma is cultured in a cell culture that produces the monoclonal antibody. The monoclonal antibody is then obtained from the cell culture.

The present invention also relates to a method of determining whether a human subject is susceptible to a type of cancer characterized by positive expression of PDEF. This method involves obtaining a tissue sample from a subject, where the tissue sample is suspected of being a cancer tumor tissue. The tissue sample is then contacted with the antibody or antigen-binding fragment thereof according to the present invention, and under conditions effective to allow for measuring the level of PDEF expression in the tissue sample. Under this method, measuring the level of PDEF expressed in the tissue sample using an immunohistochemical assay, whereby positive expression of PDEF indicates that the subject is susceptible to a type of cancer characterized by positive expression of PDEF.

Suitable tissue samples can include breast tissue, prostate tissue, ovarian tissue, endometrial tissue, colon tissue, and cervical tissue. This method can be used with regard to breast cancer, prostate cancer, ovarian cancer, endometrial cancer, colon cancer, and cervical cancer.

In another aspect, the present invention relates to a method of prognostic stratification of a cancer patient for targeted therapeutic cancer treatment. This method involves obtaining a tissue sample from the cancer patient, where the tissue sample is suspected of including cancer tumor tissue. The tissue sample is contacted with the antibody or antigen-binding fragment thereof of the present invention so as to be effective to allow for measuring the level of PDEF expression in the tissue sample. The level of PDEF is then measured in the tissue sample using an immunohistochemical assay, whereby positive expression of PDEF indicates that the patient is in need of therapeutic treatment for a type of cancer characterized by positive expression of PDEF. Thereafter, the patient is provided with the therapeutic treatment effective for the type of cancer characterized by positive expression of PDEF. This method can be used to test tissue samples from breast tissue, prostate tissue, ovarian tissue, endometrial tissue, colon tissue, and cervical tissue, as they related to breast cancer, prostate cancer, ovarian cancer, endometrial cancer, colon cancer, and cervical cancer.

Additionally, in recent years "prognostic gene signatures" have been identified that predict clinical outcome for breast cancer patients (24). Two of these gene signatures, including Oncotype DX (25) and MammaPrint (26), appear robust and are presently being marketed for prognostic evaluation in breast cancer. An important limitation of the gene expression signatures is that their roles in determining prognosis is not completely understood, i.e., what tumor characteristics (e.g.

tumor growth, invasiveness, metastasis, and/or survival) are being affected by specific genes in the signature.

Consequently, these aforementioned prognostic gene signatures do not offer the opportunity to develop novel therapeutics targeted to individual genes in the signature. In contrast, individual biomarkers, when validated, allow the development of highly specific targeted therapeutics with minimal side effects. In this regard, ER and Her2/neu in breast cancer and androgen receptor (AR) in prostate cancer are not only prognostic/predictive biomarkers, but they also serve as useful targets of specific novel treatment approaches, i.e., tamoxifen and aromatase inhibitors that inhibit ER function; Herceptin that inhibits Her2/neu function, and androgen antagonists that inhibit AR function. Similar to these biomarkers, PDEF is expected to be a useful prognostic/predictive marker and a novel target for developing specific drugs or vaccines against breast, prostate, and ovarian cancers, and such specific targeting of cancer is expected to show minimal side effects.

An example of steps involved in the use of anti-PDEF antibody for determining prognosis and for stratification of a breast cancer patient for treatment selection, is as follows:

Step 1: A breast cancer patient arrives in the clinic, undergoes surgery to remove cancer.

Step 2: A pathologist prepares the tumor sample for standard immunohistochemistry for evaluating ER and Her2/neu expression. If the tumor is ER+, the tumor will be further screened with anti-PDEF antibody to determine PDEF status.

Step 3: If the tumor is ER+ PDEF−, i.e., stains positive for ER and negative for PDEF, the patient's prognosis is good and patients will receive Tamoxifen treatment. If, on the other hand, the tumor is ER+ PDEF+, i.e., stains positive for both ER and PDEF, the prognosis is bad and patient will receive Tamoxifen and a new drug or vaccine targeted to PDEF.

The above example is restricted only to ER+ tumors, but it is contemplated by the present invention that such a method can be used for Her2/neu+ luminal breast tumors, where high expression of PDEF will also predict poor prognosis and similarly allow stratification of patients to receive either Herceptin alone or Herceptin and a PDEF-targeted drug or vaccine in case of low PDEF and high PDEF, respectively. These steps also apply to patients with AR+ breast tumors in which PDEF is expressed in all tumors.

Similar considerations will apply for ovarian cancer patients and for prostate cancer patients, except that PDEF-based vaccines may not be useful for prostate cancer patients, since data generated with mice show that males respond poorly to Pse (prostate specific Ets, mouse homologue of PDEF) vaccine, perhaps due to tolerance to Pse as a self antigen because of its strong expression in normal prostate. For prostate cancer patients, small molecule inhibitor based drugs will be useful.

The present invention also relates to a method of treating or preventing a disease characterized by growth of tumor cells expressing PDEF. This method involves administering to a subject a vaccine according to the present invention, thereby inducing T cell immunity that inhibits growth of tumor cells that express PDEF.

The present invention also relates to a method of treating or preventing a disease characterized by growth of tumor cells expressing PDEF, by administering to a subject a small molecule inhibitor that inhibits PDEF expression in tumors cell, thereby inhibiting growth of tumor cells that express PDEF. A suitable small molecule inhibitor can include, for example, an antisense oligonucleotide including at least 15 nucleotides and having a nucleotide sequence that is complementary to at least 15 nucleotides of an encoding nucleotide sequence of a PDEF fragment. The PDEF fragment encoded by the nucleotide sequence can encode an amino acid sequence selected from the group consisting of SEQ ID NO:2, SEQ ID NO:3, and SEQ ID NO:4; (ii) an amino acid sequence having at least 5 continuous residues from SEQ ID NO:2, SEQ ID NO:3, or SEQ ID NO:4; or (iii) two or more amino acid sequences having at least 5 continuous residues from SEQ ID NO:2, SEQ ID NO:3, and/or SEQ ID NO:4.

In one aspect, the present invention relates to a method for detecting pre-existing spontaneous antibody response to human PDEF in a serum sample of a subject. This method involves contacting the serum sample with peptides corresponding to SEQ ID NO:2, SEQ ID NO:3, and/or SEQ ID NO:4 under conditions such that an immunocomplex forms. The presence of the immunocomplex is then detected, where such detection indicates pre-existing spontaneous T cell response to human PDEF in a serum sample of the subject.

In another aspect, the present invention relates to a method for detecting pre-existing spontaneous T cell response to human PDEF in a sample of blood cells of a subject. This method involves contacting the sample of blood cells with overlapping peptides of at least 8 continuous residues of the amino acid sequences corresponding to SEQ ID NO:2, SEQ ID NO:3, and/or SEQ ID NO:4. T cell proliferation by enzyme-linked immunospot (ELIspot) assay is then measured, where positive detection indicates pre-existing spontaneous antibody response to human PDEF in a sample of blood cells of a subject.

The present invention also relates to a method for boosting immunity of a cancer patient to a cancer disease associated with positive expression of PDEF. This method involves obtaining a tissue sample from the cancer patient, where the tissue sample is suspected of including cancer tumor tissue. The tissue sample is contacted with the antibody or antigen-binding fragment thereof according to the present invention, under conditions effective to allow for measuring the level of PDEF expression in the tissue sample. The level of PDEF expressed in the tissue sample is measured using an immunohistochemical assay, whereby positive expression of PDEF indicates that the patient is in need of an additional immunization against PDEF. The patient is then tested for any pre-existing antibody or T cell response against PDEF, and finding of such response makes patient a better candidate for receiving vaccine treatment. The patient is then provided with a vaccine of the present invention under conditions effective to boost immunity of the cancer patient to the cancer disease associated with positive expression of PDEF. As contemplated by this method, the tissue sample can be selected from the following tissues, without limitation: breast tissue, ovarian tissue, endometrial tissue, colon tissue, and/or cervical tissue. Further, this method is effective in boosting the immunity of a cancer patient to one of the following cancer diseases associated with positive expression of PDEF: breast cancer, ovarian cancer, endometrial cancer, colon cancer, and/or cervical cancer.

The present invention is illustrated by the following examples.

EXAMPLES

The following examples are intended to illustrate particular embodiments of the present invention, but are by no means intended to limit the scope of the present invention.

Certain of the Examples presented herein below include experimental data performed by the inventor and published in the following articles: (i) Sood, A. K., Saxena, R., Groth, J. et al., "Expression Characteristics of PDEF Support a Role in Breast and Prostate Cancer Progression," *Hum. Pathol.* 38(11):1628-1638 (2007) and (ii) Rodabaugh, M. D., et al., "Prostate Derived Ets Factor is Overexpressed in Serous Epithelial Ovarian Tumors," *Int. J. Gynecol. Pathol.* 26(1):10-15 (2007), the entire disclosures of which are hereby incorporated by reference in their entirety.

Example 1

Antibody Production: Anti-PDEF Antibody

A Blast homology search for PDEF protein sequence showed significant homology (60-74% amino acid residue homology, as shown in FIG. 1C) with the C-terminal DNA binding Ets domain of PDEF with that of other Ets factors. Also, there is significant homology in the Pointed domain of PDEF with other human Ets factor proteins (shown in FIG. 1B). In contrast, the N-terminal segment of PDEF comprising residues 1 to 104 (PDEF-1-104) revealed homology only to PDEF (shown in FIG. 1A). Therefore, this PDEF-1-104 segment was selected for producing polyclonal antibodies in rabbits. Briefly, the cDNA encoding the N-terminal 1 to 104 amino acids was PCR-amplified and subcloned into the bacterial expression vector pET15b (Novagen, Madison, Wis.) at the Nde I site. After confirmation of the orientation and sequence, *E. coli* BL21 (DE3) cells were transformed by the resultant pET15b-PDEF-1-104 plasmid. The cells were induced by 1 mM IPTG and PDEF protein was purified from bacterial lysates by affinity chromatography on a Ni-NTA column. Further purification on MonoQ column (Amersham, Piscataway, N.J.) provided pure preparations of the PDEF-1-104 peptide. The purified PDEF-1-104 peptide was used for production of polyclonal antibodies in rabbits. Briefly, two New Zealand white rabbits each were immunized by intradermal injection of 100 μg of PDEF-1-104 protein emulsified in complete Freund's adjuvant. This was followed by three booster injections with 150 μg protein in incomplete Freund's adjuvant at two-week interval and the 4$^{th}$ injection at 6 weeks following the third boost. Serum was collected and tested for reactivity by ELISA and Western blot assays using purified PDEF protein as an antigen. PDEF antibodies were further purified on a PDEF-full-length protein-immobilized affinity column (Pierce, Rockford, Ill.).

Example 2

Specificity of Anti-PDEF Antibody by Western Blotting and Immunohistochemistry

As shown in Panel A of FIG. 2, anti-PDEF antibody reacted specifically with a 46 kD band in the MCF-7 breast tumor cell line, but not with the SKBR3 breast tumor cell line or the non-breast tumor cell lines Hela and U937. Also, the antibody reacted strongly with recombinant PDEF protein run as control. Further, the antibody showed specific nuclear staining of tumor cells in the MCF-7 breast tumor cell line (FIG. 2, panel B), and its prior incubation with PDEF 1-104 peptide eliminated the staining. Furthermore, screening of the tissue sections from a primary breast carcinoma (FIG. 2, Panel C) and a primary prostate carcinoma (FIG. 2, Panel D) showed specific staining of the epithelial tumor cells, a result consistent with epithelial cell specific expression of PDEF mRNA.

Example 3

Figure 3:
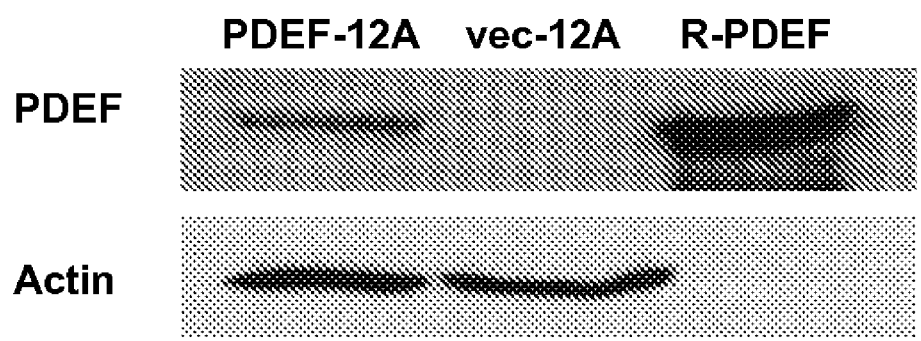
FIG. 3 illustrates additional testing of the specificity of anti-PDEF antibody by Western blotting. Upper panel shows reactivity with PDEF protein from PDEF-transfected MCF-12A cells (left panel) and with recombinant PDEF protein (right panel). No reactivity was observed with vector-transfected MCF-12A cells.

Transfection of PDEF-Lacking MCF12-A Cell Line with PDEF Induces Reactivity with Antibody Specificity of the anti-1-104 antibody for PDEF was further tested by transfecting PDEF-lacking MCF-12A cell line with PDEF expression plasmid. As shown in FIG. 3, only the PDEF-transfected MCF-12A cells but not vector-transfected MCF-12A cells showed reactivity with our antibody.

Example 4

Figure 4:
FIG. 4 illustrates additional testing of the specificity of anti-PDEF antibody by immunohistochemistry using normal human tissues. PDEF protein expression was analyzed in a panel of normal human tissues. Photomicrographs show strong expression of PDEF in normal prostate tissue and the normal trachea/bronchus tissue (FIG. 4A).
Figure 4:
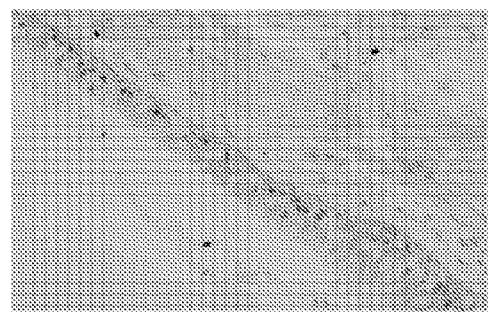

Screening of Normal Human Tissues Further Validates PDEF Specificity of the Antibody of the Present Invention Previous work from Inventor's lab showed highly restricted expression of PDEF mRNA in normal human tissues that was primarily limited to normal prostate and trachea (3). To determine whether PDEF protein expression corresponds with PDEF mRNA expression, tissue sections from a panel of normal human tissues were screened for PDEF protein expression using Inventor's antibody. The data showed that strong expression of PDEF protein was present in the normal prostate tissue (FIG. 4, panel A) and a somewhat weaker expression in the normal bronchus/trachea tissue (FIG. 4, panel B). Other normal human tissues including brain, heart, kidney, liver, lung, lymph nodes, ovary, pancreas, placenta, skeletal muscle, skin, spleen, stomach and thymus stained negative for PDEF protein expression. These results are in agreement with the corresponding data on PDEF mRNA expression in the respective tissues (3); and further validate the specificity of the anti-PDEF antibody of the present invention.

Example 5

Figure 5:
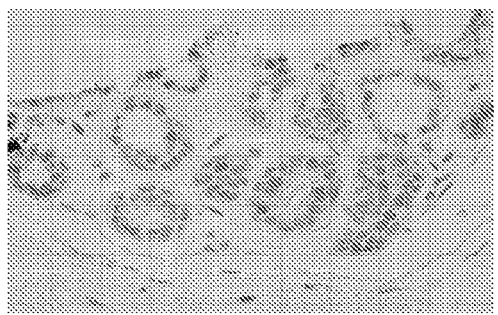
FIG. 5 illustrates PDEF expression in matched pairs of benign breast and breast tumor tissues from individual patients. The upper and lower pairs of photomicrographs show representative PDEF staining in matched samples of adjacent benign breast versus breast tumor tissues from two patients. Increased staining in tumor tissues is seen in comparison to benign tissues. Results for PDEF staining in matched pairs from additional nine patients are shown in Table 1. These results are also similar to those previously reported for PDEF mRNA expression in matched samples of adjacent benign and tumor tissues from breast cancer patients (3). Together, the results shown in FIGS. 4 and 5 show correspondence between PDEF mRNA and protein in normal human normal tissues and in human breast tumors, and rigorously demonstrate the specificity of the antibody of the present invention for PDEF by immunohistochemical assay.
Figure 5:
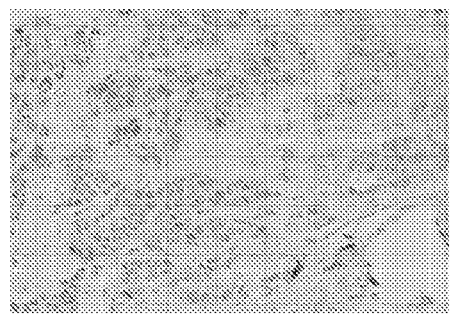
Figure 5:
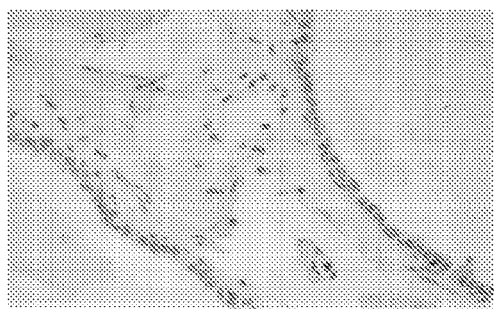
Figure 5:
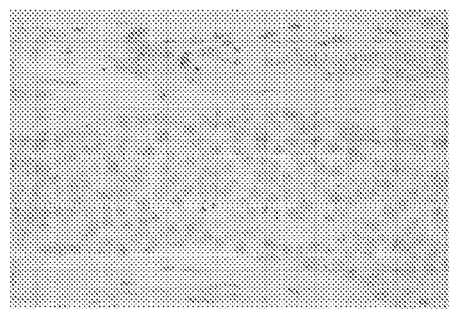
Figure 6A:
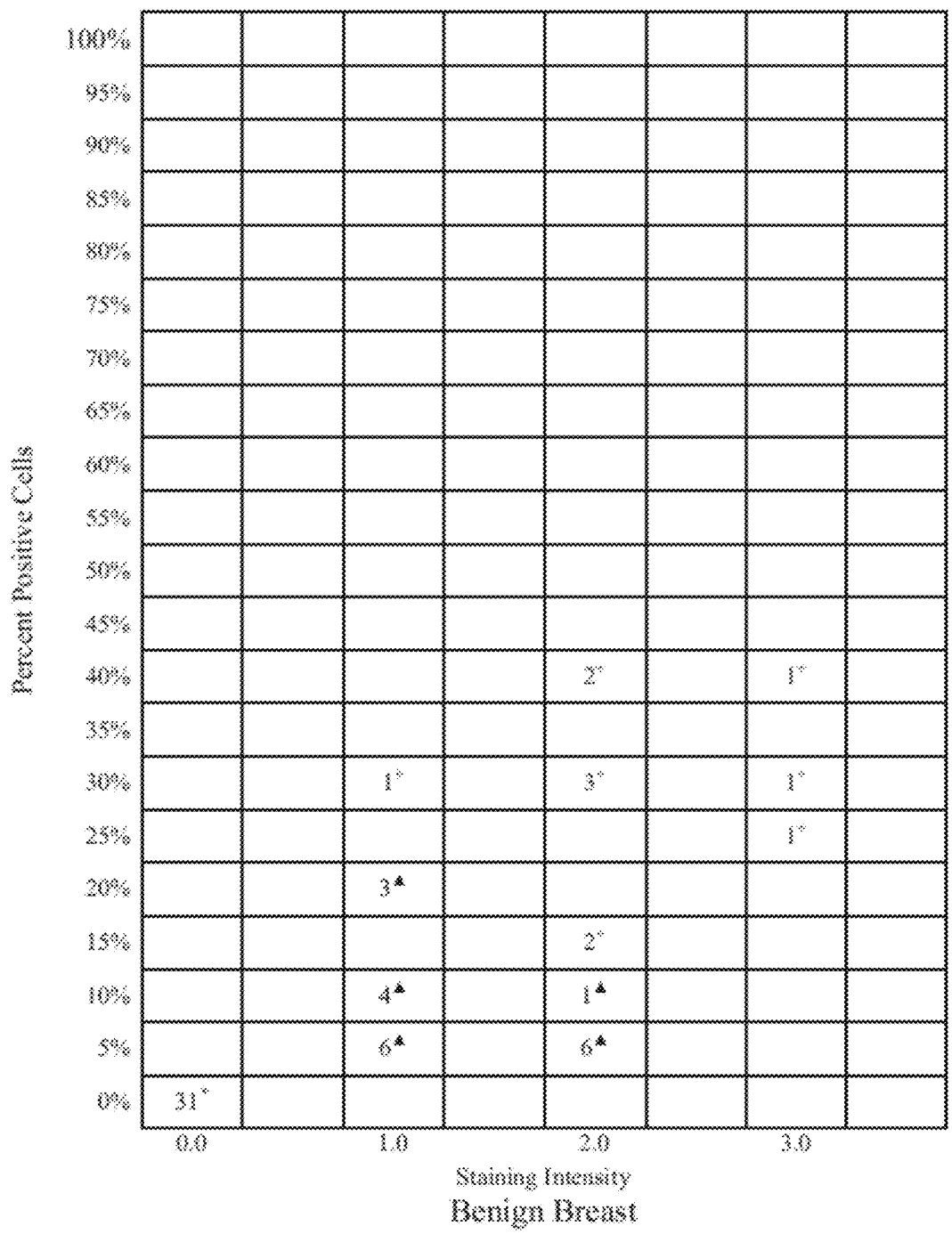
FIGS. 6A-6D illustrate the characteristics of PDEF protein expression in progression from benign breast tissue to carcinoma. PDEF expression in benign breast tissues (FIG. 6A), intraductal carcinomas (DCIS) (FIG. 6B), invasive ductal carcinomas (FIG. 6C) and invasive lobular carcinomas (FIG. 6D) was examined using the antibody described herein. Negative samples (all tumor cells lacking staining) are identified using a superscripted asterisk sign (*). The samples showing PDEF expression below thresholds are identified using a superscripted triangle sign (▲). The superscripted plus signs (+) in the graphs represent individual samples that stained above the selected thresholds and therefore scored positive for PDEF expression. The x-axis in these graphs shows different levels of staining intensity i.e. 1+, 2+ and 3+. The y-axis shows percent of positively staining cells in a given tumor sample.
Figure 6B:
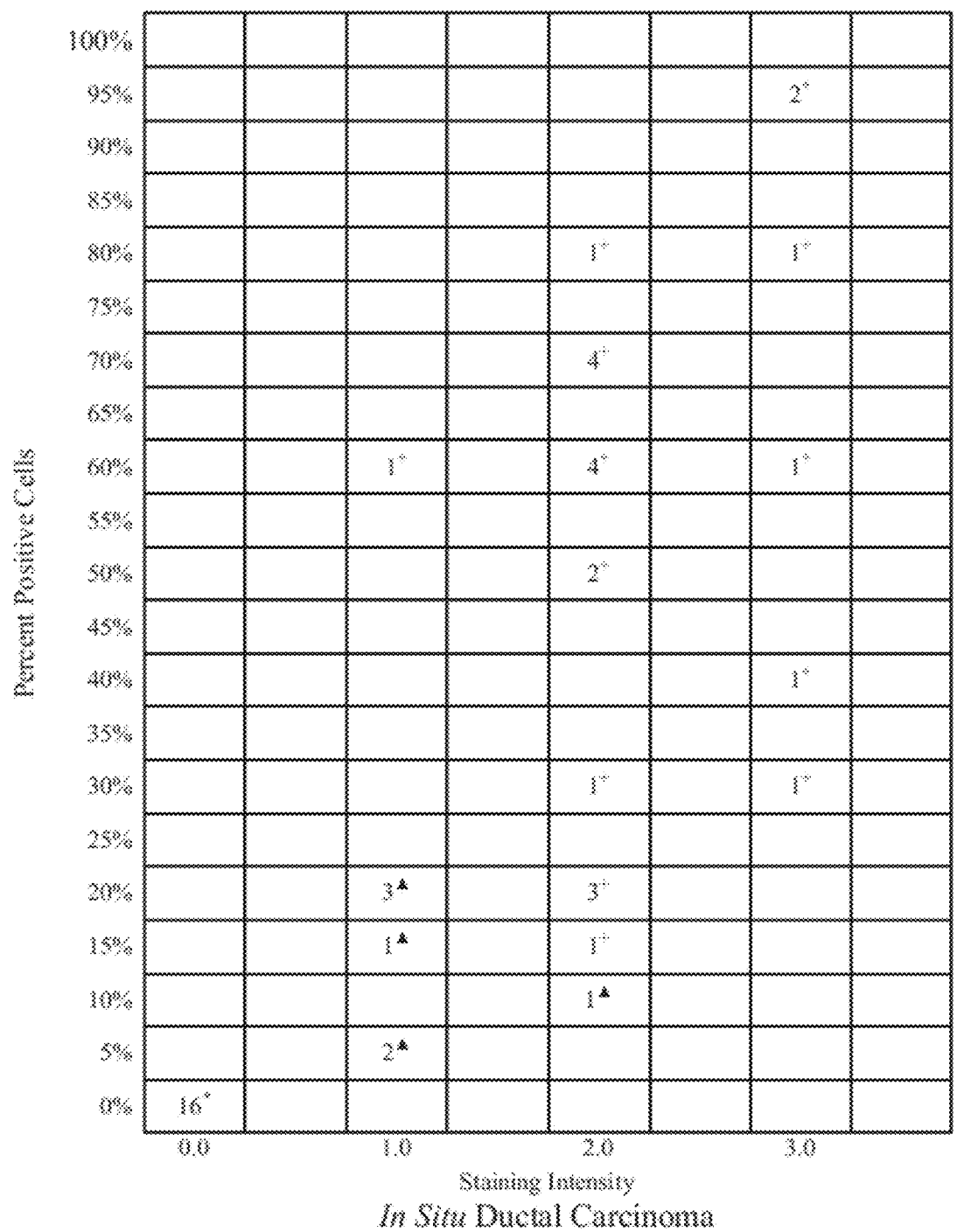
Figure 6C:
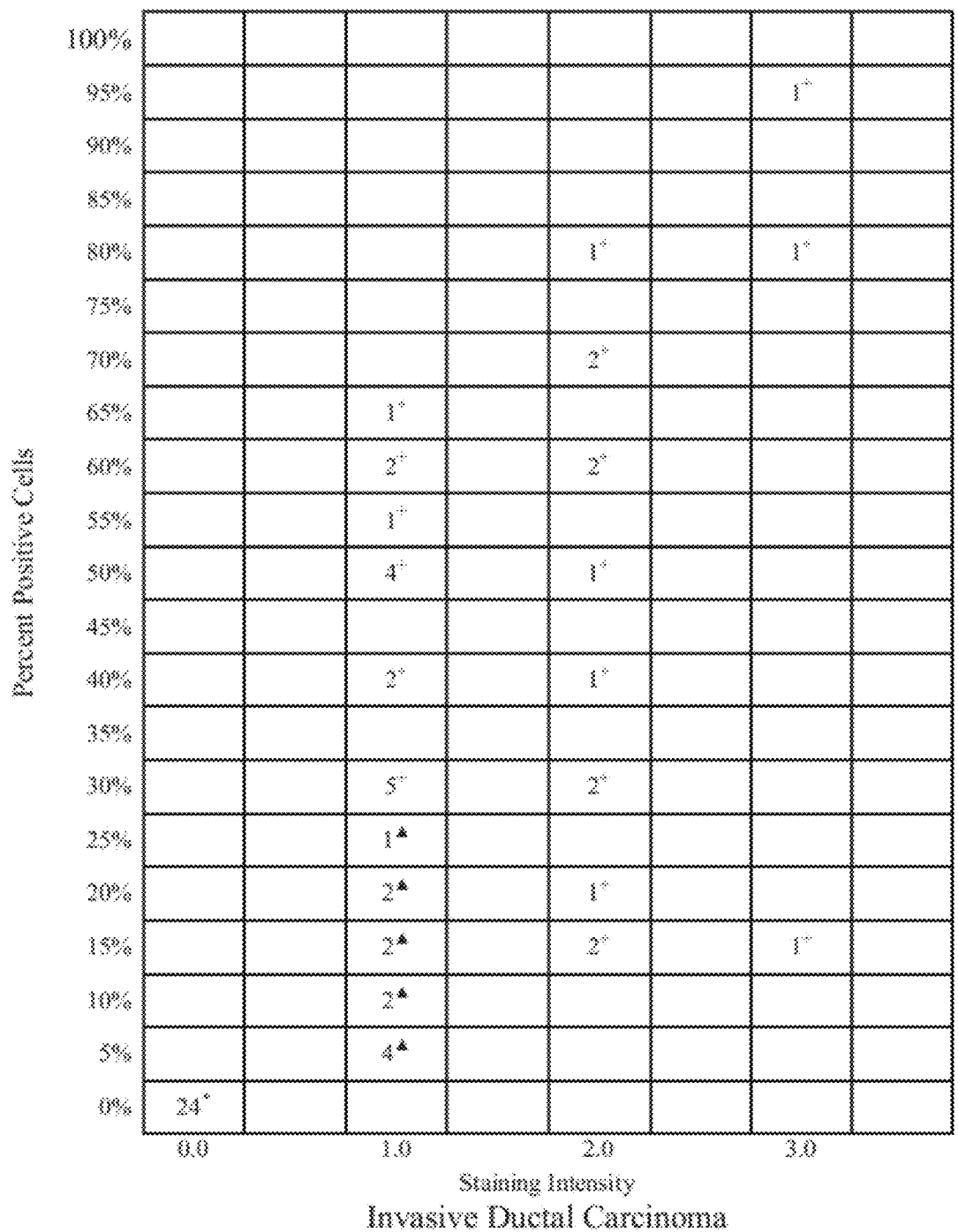
Figure 6D:
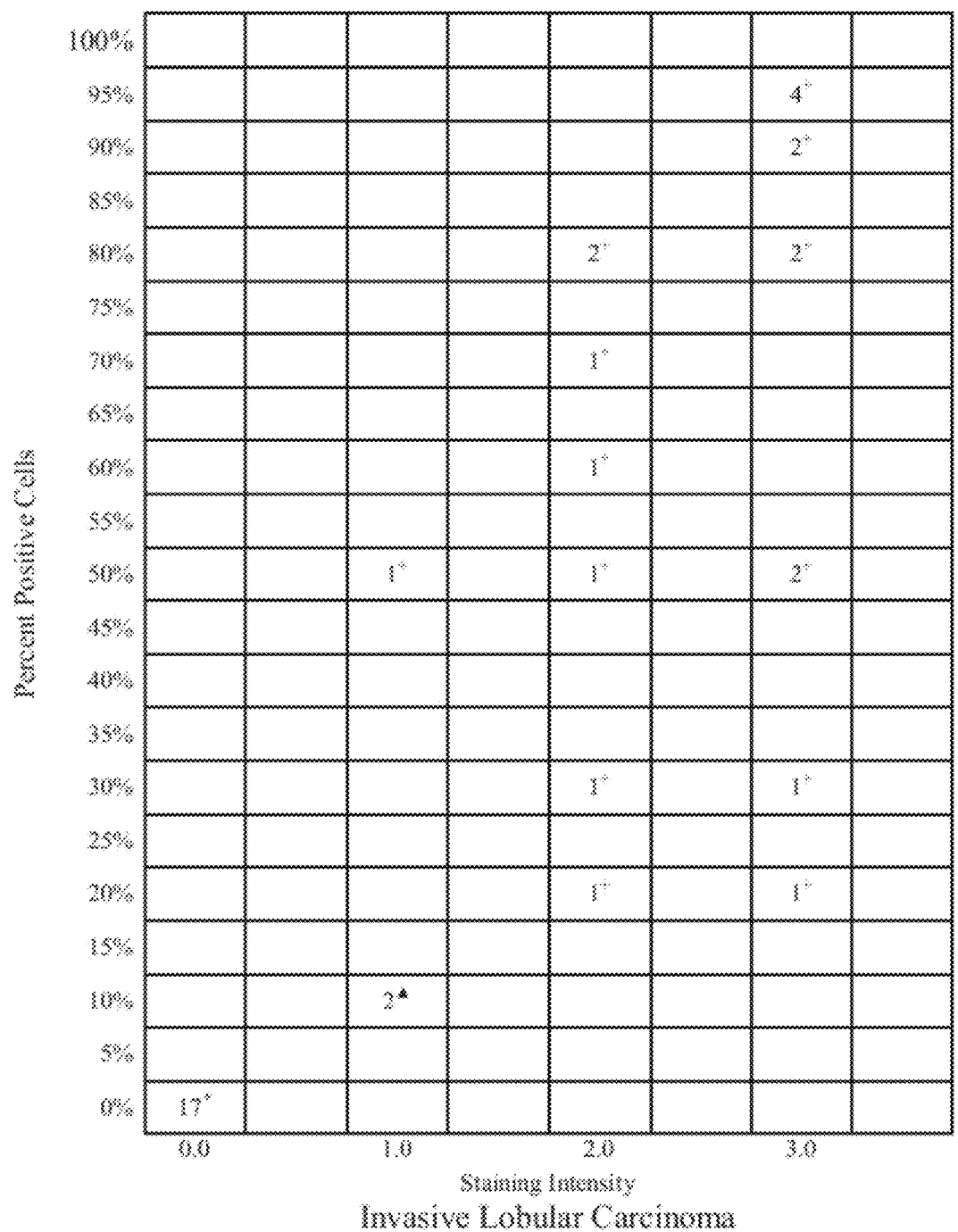

PDEF Expression in Matched Pairs of Benign Breast and Breast Tumor Tissues from Patients Previous work from Inventor's lab showed over expression of PDEF mRNA in breast tumor tissues in comparison to adjacent benign breast tissue from individual patients, and the level over expression in the tumor tissue varied from a few-fold to as much as 88-fold (3). To determine whether similar over expression of PDEF protein occurs in breast tumors, PDEF protein expression was analyzed in 9 matched pairs of adjacent benign breast and tumor tissues, by using the antibody of the present invention described herein. It was found that in 90% (8 of 9) cases, the tumors showed an increase in the number of PDEF expressing epithelial cells and/or the intensity of staining of such cells. The data are summarized in Table 1 and representative photomicrographs are shown in FIG. 5.

TABLE 1

PDEF Expression in Matched Samples of Benign Breast and Tumor Tissues

| Benign/Tumor Pair Number | PDEF Expression Characteristics (Percent Positive Cells, Intensity of Staining) | |
|---|---|---|
| | Benign | Tumor |
| 1 | 0 | 40%, 1+ |
| 2 | 0 | 20%, 2+ |
| 3 | 40%, 2+ | 60%, 2+ |
| 4 | 30%, 2+ | 5%, 1+ |
| 5 | 5%, 1+ | 30%, 3+ |
| 6 | 5%, 1+ | 20%, 2+ |
| 7 | 0 | 80%, 2+ |
| 8 | 15%, 1+ | 65%, 1+ |
| 9 | 0 | 60%, 2+ |

Together, the results shown in FIGS. 2-5 demonstrate the specificity of the anti-PDEF antibody of the present invention for PDEF, as well as its suitability for use in immunohistochemical analysis of PDEF expression in tissue sections from primary tumors from patients.

Example 6

Characteristics of PDEF Expression in Tumor Progression and Use of PDEF Expression Levels in Patient Prognosis and Patient Stratification for Treatment The validated PDEF antibody of the present invention was used to determine the characteristics of PDEF protein expression in benign tissues and in primary tumor samples from breast, prostate, and ovarian tumors from cancer patients. The results are described below.

PDEF expression is increased in progression from benign breast to ductal carcinoma in situ (DCIS) and increased expression is maintained in invasive carcinomas: Using the above antibody of the present invention, tissue micro arrays (TMAs) of breast tissues were screened for PDEF expression. The data from this screening are presented in FIG. 6 and are summarized below.

In benign breast tissue samples, 18% (11 of 62) scored positive for PDEF expression. Of the remaining samples, 20 of 62 (32%) showed expression levels below the selected thresholds, and 31 of 62 (50%) lacked any detectable PDEF expression.

For DCIS, 50% (23 of 46) of the samples scored positive for PDEF expression, another 7 (15%) stained below the thresholds, and the remaining 16 of 46 (35%) showed no detectable staining.

A similar analysis of invasive ductal carcinoma (IDC) showed that 46% (30 of 65) of the invasive tumors were positive for PDEF expression. Of the remaining samples, 17% (11 of 65) showed staining below the thresholds and 24 of 65 (37%) lacked detectable staining.

In invasive lobular carcinoma (ILC), 51% (20 of 39) of the samples scored positive for PDEF expression, another 5% (2 of 39) stained below the thresholds, and the remaining 44% (17 of 39) were negative.

In summary, the data presented in FIG. 6 show that, whereas 18% of benign breast tissues scored positive for PDEF, samples from DCIS, IDC, and ILC showed a much higher percentage of PDEF positive tumors, i.e., 50%, 46% and 51% of the screened samples, respectively.

Example 7

Progressively Increasing Fractions of Benign Prostate Tissue, PIN, and Prostate Carcinoma Samples Score Positive for PDEF Expression Using the anti-PDEF antibody of the present invention, TMAs of prostate tissues were also stained and scored for PDEF expression. The data are presented in FIG. 7 and are described below.

In the benign prostate tissues from cancer patients, 27% (79 of 290) scored positive for PDEF expression. Of the remaining samples, 24 of 290 (9%) stained below the selected thresholds and another 187 of 290 (64%) lacked detectable PDEF expression.

For PIN samples, 36 of 109 (33%) scored positive for PDEF expression. Of the remaining, 9 of 109 (8%) stained below the thresholds and 64 out of 109 (59%) showed no detectable staining.

A similar analysis of prostate carcinomas revealed that 40% (92 of 230) of the invasive carcinomas were positive for PDEF expression, another 11% (25 of 230) showed staining below thresholds, and the remaining 113 out of 230 (49%) samples lacked detectable staining.

Figure 7A:
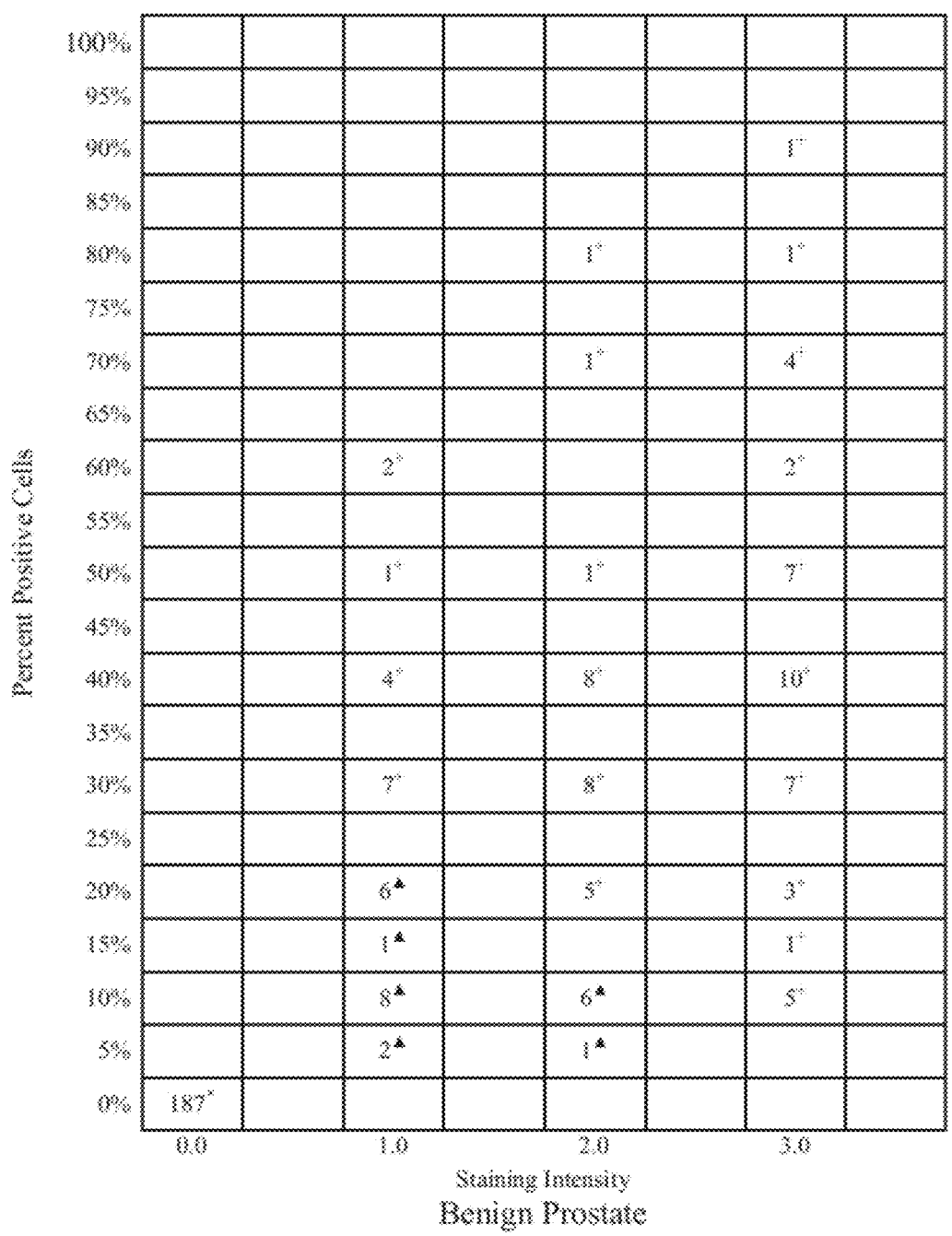
FIGS. 7A-7C illustrate the characteristics of PDEF protein expression in progression from benign prostate tissue to carcinoma. PDEF expression in samples from benign prostate tissues (FIG. 7A), prostate intraepithelial neoplasias (PIN) (FIG. 7B) and prostate carcinomas (FIG. 7C) was examined using the antibody described herein. Negative samples (all tumor cells lacking staining) are identified using a superscripted asterisk sign (*). The samples showing PDEF expression below thresholds are identified using a superscripted triangle sign (▲). The superscripted plus signs (+) represent individual samples that stained above the selected thresholds and therefore scored positive for PDEF expression. The x-axis in these graphs shows different levels of staining intensity i.e. 1+, 2+ and 3+. The y-axis shows percent of positively staining cells in a given tumor sample.
Figure 7B:
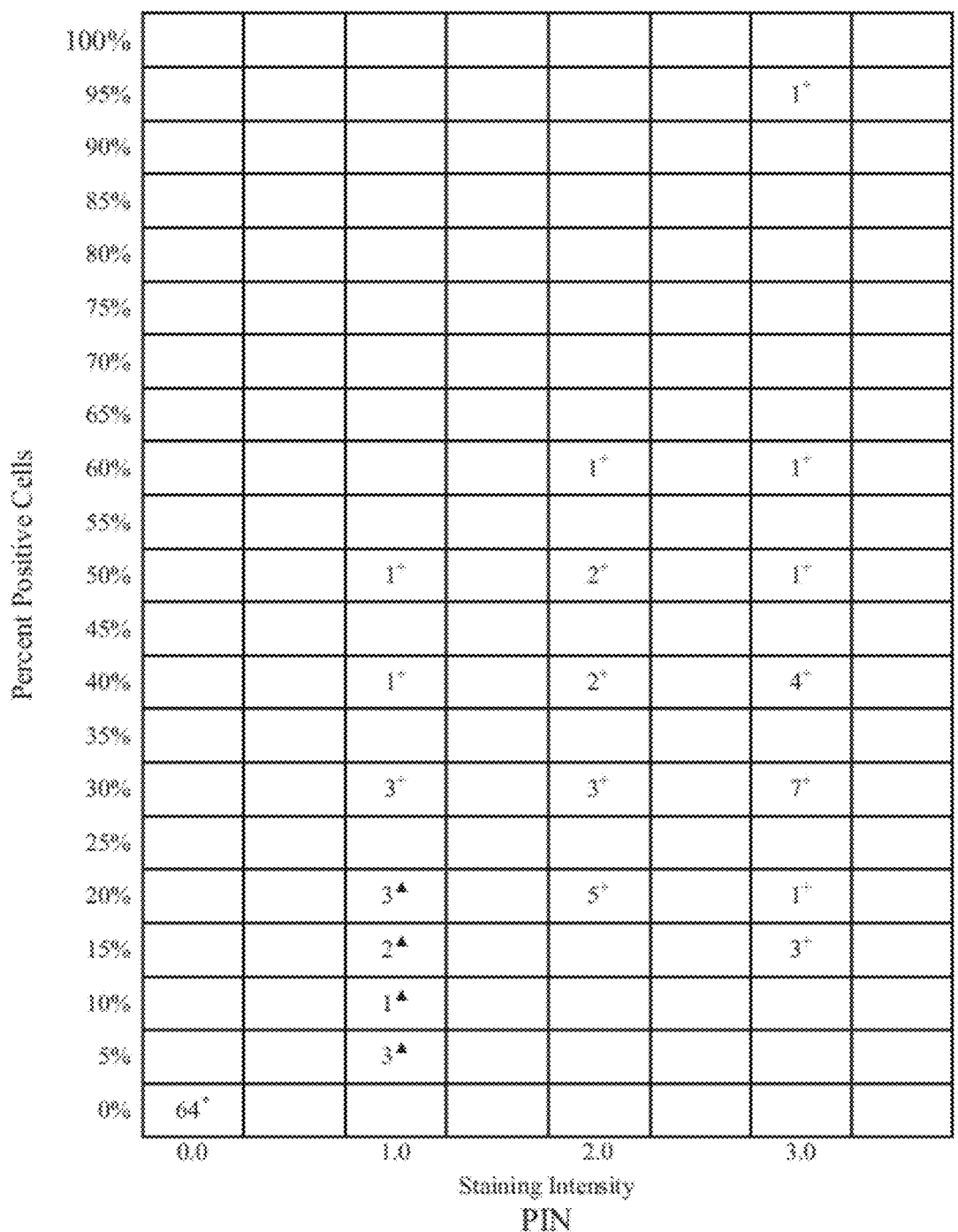
Figure 7C:
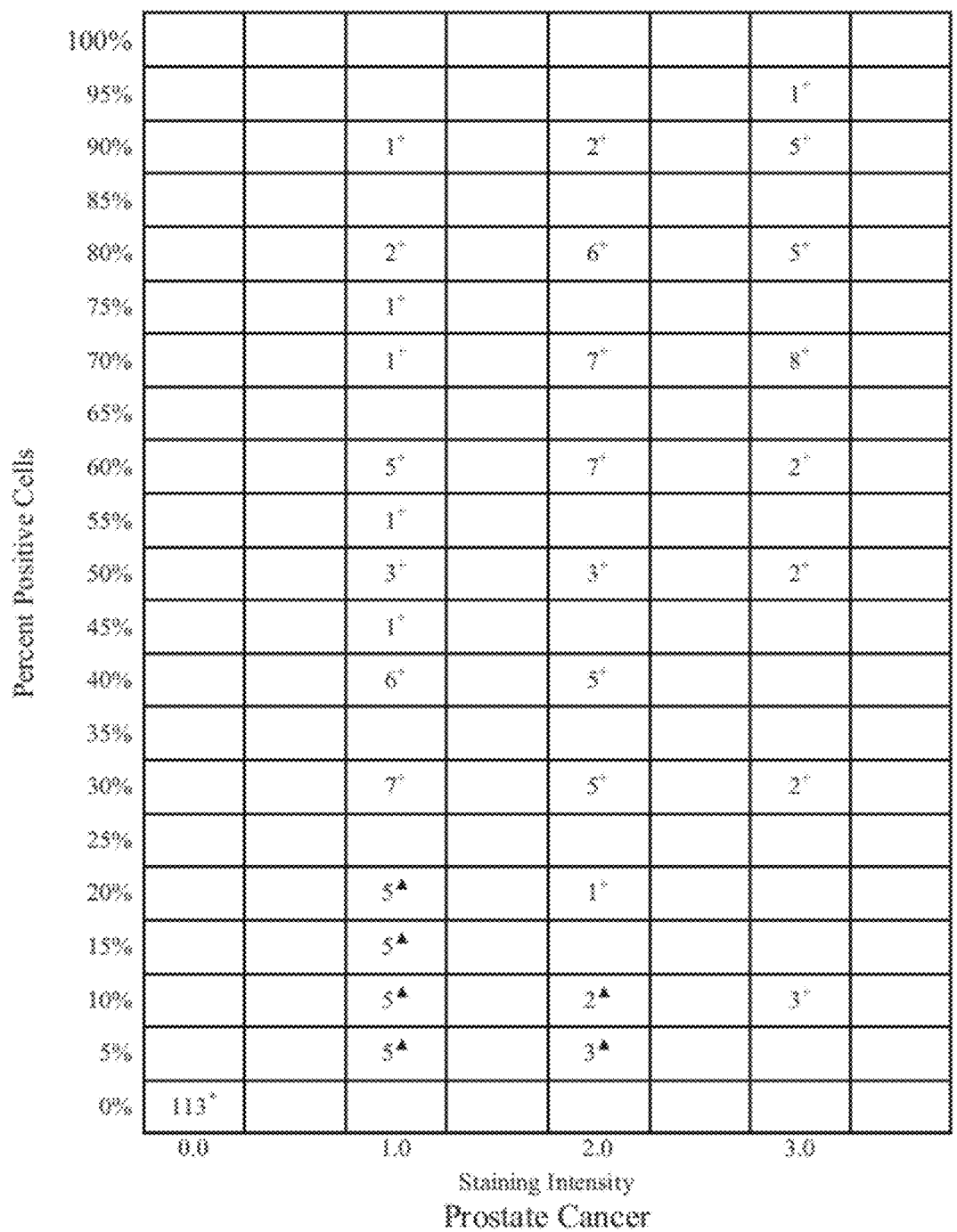

In summary, the data presented in FIG. 7 support the following points: (i) increasingly higher percentage of samples scored positive for PDEF expression in progression from benign prostate tissues (27% of samples positive), to PIN lesions (33% of samples positive), and to prostate carcinomas (40% of samples positive); and (ii) prostate carcinomas generally showed a higher percentage of cells staining positive for PDEF in comparison to PIN or benign tissue samples.

Example 8

Analysis of PDEF Expression in Matched Samples of Cancer Versus Benign, Cancer Versus PIN, and PIN Versus Benign Showed Frequent Increased PDEF Expression in Prostate Cancer To further understand the characteristics of PDEF protein expression in benign prostate and prostate carcinomas, PDEF expression was analyzed in matched samples of prostate cancer and adjacent benign tissue or PIN. Overall, this analysis included 101 matched samples of cancer versus (v/s) benign, 41 matched samples of cancer v/s PIN, and 45 matched samples of PIN v/s benign. The data are compiled in Table 2. As shown in this Table 2, in 68% (68 of 101) of the matched cancer v/s benign pairs, cancer specimens expressed higher levels of PDEF than the adjacent benign prostate tissues. Similarly, in 70% (28 of 41) of the matched cancer v/s PIN pairs, cancer showed higher PDEF expression than PIN. In contrast, in PIN versus benign comparison, only 42% (19 of 45) PIN lesions showed higher PDEF expression than the matched benign glandular tissues.

TABLE 2

PDEF Expression in Prostate Tissue:
Matched Samples of Cancer v/s Benign,
Cancer v/s PIN, and PIN v/s Benign

| Type of Match X v/s Y | Number of matched samples | Number of samples with more* PDEF in X | Number of samples with more* PDEF in Y | P value |
|---|---|---|---|---|
| Cancer v/s benign | 101 | 68 (68%) | 33 (32%) | 0.0006 |
| Cancer v/s PIN | 41 | 28 (70%) | 13 (30%) | 0.0275 |
| PIN v/s benign | 45 | 19 (42%) | 26 (58%) | 0.3713 |

*More PDEF reflects higher percent of PDEF-positive epithelial cells or higher intensity of staining or both.

In summary, the combined data from FIG. 7 and Table 2 show that PDEF expression is frequently increased in the progression from benign prostate to cancer and from PIN to cancer. In contrast, there appeared to be no significant change in PDEF expression in progression from benign prostate to PIN.

Example 9

Figure 8:
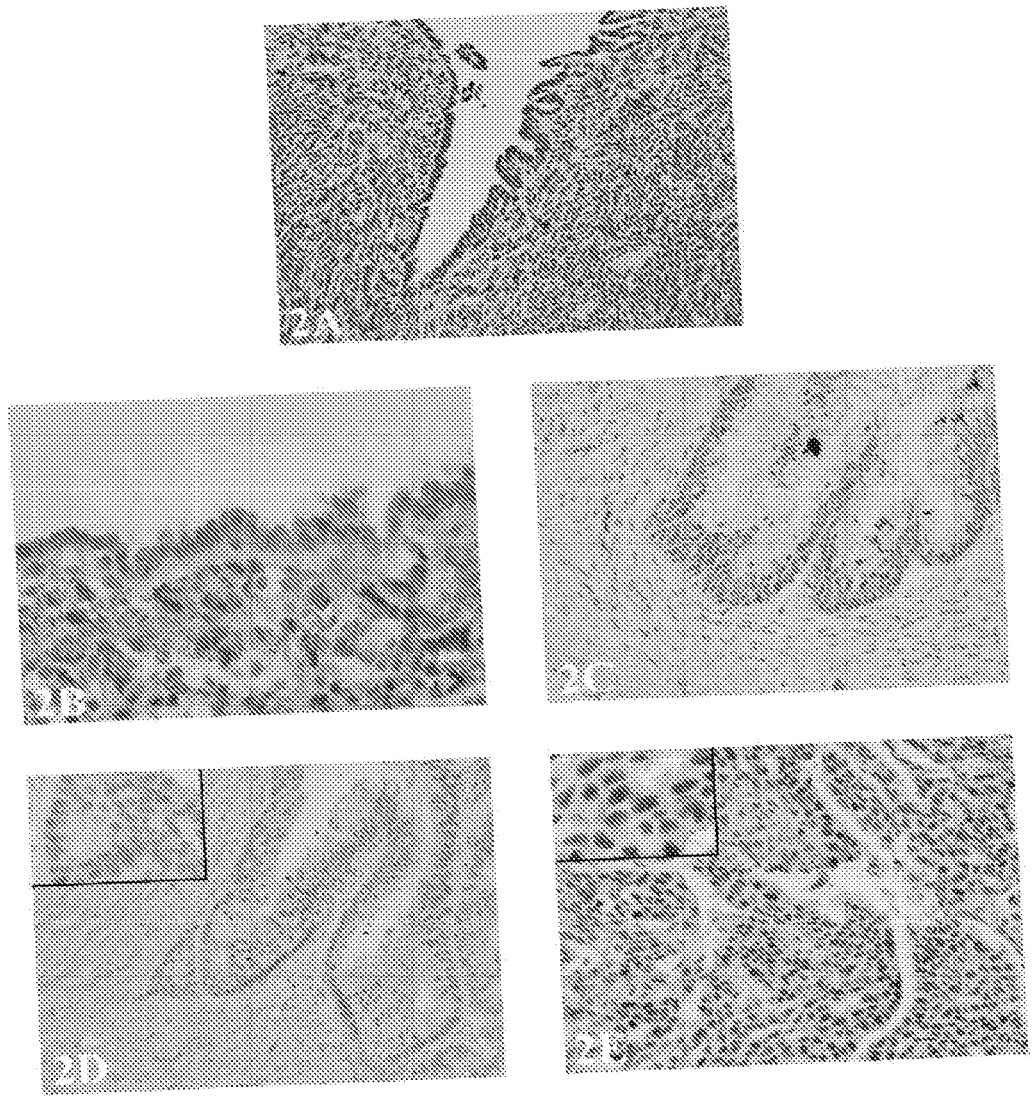
FIG. 8 illustrates the characteristics of PDEF expression in progression from benign ovaries to carcinoma. PDEF expression in normal ovaries, cystademomas and in different types and stages of ovarian neoplasia was examined using the antibody described here. Panel 2A, negative staining of normal ovary; Panel 2B, negative staining of cystadenoma; Panel 2C, positive PDEF expression in a low malignant potential tumor; Panel 2D, positive PDEF expression in stage I serous ovarian cancer and Panel 2E, positive PDEF expression in advanced stage serous ovarian cancer.

PDEF Protein Expression is Undetectable in Normal Ovaries and Cyst Adenomas and Frequently Increased in Tumors of Low Malignant Potential as Well as in Early and Late Stage Epithelial Ovarian Carcinomas and Peritoneal Metastases Using the antibody of the present invention, the various ovarian normal and tumor tissue samples were stained for PDEF expression. The representative photomicrographs for each sample type are shown in FIG. 8. A brief description of the results is provided below.

All 12 samples of normal ovaries lacked detectable staining for PDEF expression. One representative photomicrograph is shown in Panel 2A.

Similarly, all 10 cases of benign serous adenoma were negative; a representative photomicrograph is shown in Panel 2B.

In ovarian tumors of low malignant potential, 6 of 17 (35%) cases scored positive for PDEF expression. The remaining cases lacked detectable staining or stained weakly, and hence were scored negative. A representative photomicrograph is shown in Panel 2C.

In early stage ovarian cancer, 5 of 19 (27%) cases were scored positive for PDEF expression and the remaining scored as negative. Again, a representative photomicrograph is shown in Panel 2D.

Similarly, in the 15 cases of advanced stage ovarian cancer, each of the primary ovarian tumors and its correlating peritoneal metastasis was evaluated for PDEF expression. In 10 (67%) of these cases, both the primary tumor and peritoneal metastases were negative for PDEF expression. Of the remaining 5 (33%) cases that scored positive for PDEF expression, one case stained similarly, while in another case the primary tumor stained more strongly and with higher percentage of positive tumor cells than the peritoneal metastases. In the remaining three cases, the peritoneal metastases stained more strongly and with higher percentage of positive tumor cells than the primary tumor. The staining of the early and advanced cases of ovarian cancer is represented by photomicrograph in Panels 2D and 2E. These results are also consistent with a role for PDEF in ovarian tumor progression.

Example 10

Figure 9:
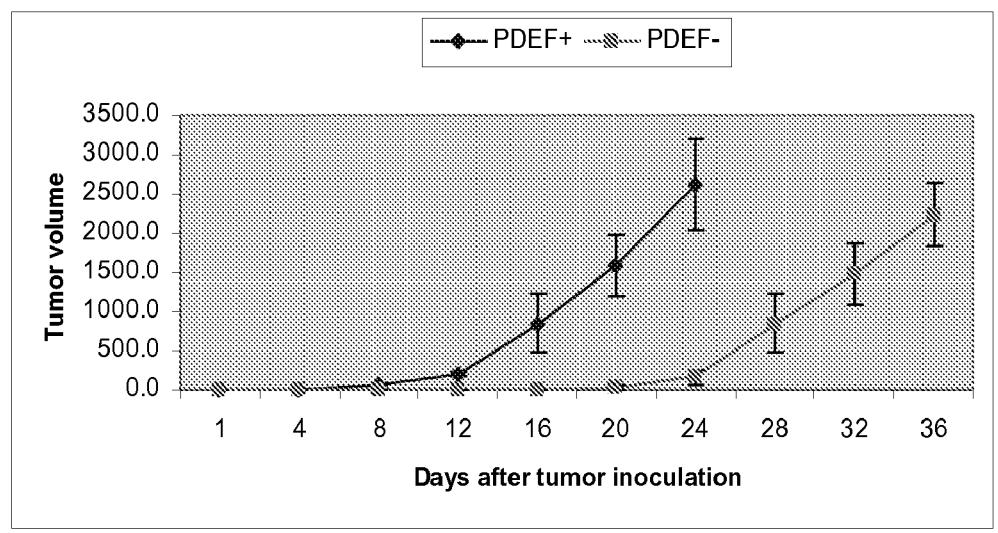
FIG. 9 illustrates enhanced tumorigenicity of PDEF expressing MCF-12 A cells. $10^6$ cells of PDEF-lacking (PDEF−) and PDEF-expressing (PDEF+) MCF-12A cells were injected s.c. into groups of 3 SCID mice each and tumor growth monitored. The tumor volume (mm3) at various time points is the average for 3 mice from each group.

Induced Expression of PDEF in Low-Tumorigenic MCF-12A Breast Cell Line Enhances its Tumorigenic Growth in Immunodeficient Mice The frequent over expression of PDEF in breast tumors raised the question whether PDEF has a direct role in breast tumor development. To test this idea, the low-tumorigenic MCF-12A cell line (that lacks PDEF) was transfected with PDEF expression plasmid, and found that PDEF-expressing MCF-12A cells form progressively growing tumors with faster kinetics, i.e., about 10 days in advance of the parental PDEF-negative MCF-12A cells (see FIG. 9). These data show a critical role for PDEF in breast tumor development, and further support a role for PDEF in breast tumor progression.

Example 11

High PDEF Expression Predicts Poor Overall Survival for Patients with ER+ Breast Cancer To seek independent evidence into the role of PDEF in breast cancer, the GEO and Oncomine databases (8) that contain the gene expression profiling and clinical outcome data from several previously published studies (9-14) were searched, looking for any correlation between PDEF expression levels and clinical outcome. Due to their adequate numbers, only ER+ breast cancer cases were included in this analysis. As shown in FIG. 10, in three independent datasets (9-11) high PDEF expression was associated with poor overall survival for patients. However, a similar analysis of three other datasets (12-14) containing clinical data on relapse and metastases showed no correlation between high PDEF expression and early tumor relapse or distant metastases (12-14). Nevertheless, significant correlation between high PDEF expression and poor overall survival for patients in three separate datasets provided crucial evidence for an important role for PDEF in breast cancer progression, and these results validate PDEF as a novel prognostic/predictive marker in breast cancer and a target for developing novel therapeutics against this cancer.

Example 12

PDEF in Pathogenesis of Luminal Breast Cancer

Figure 11:
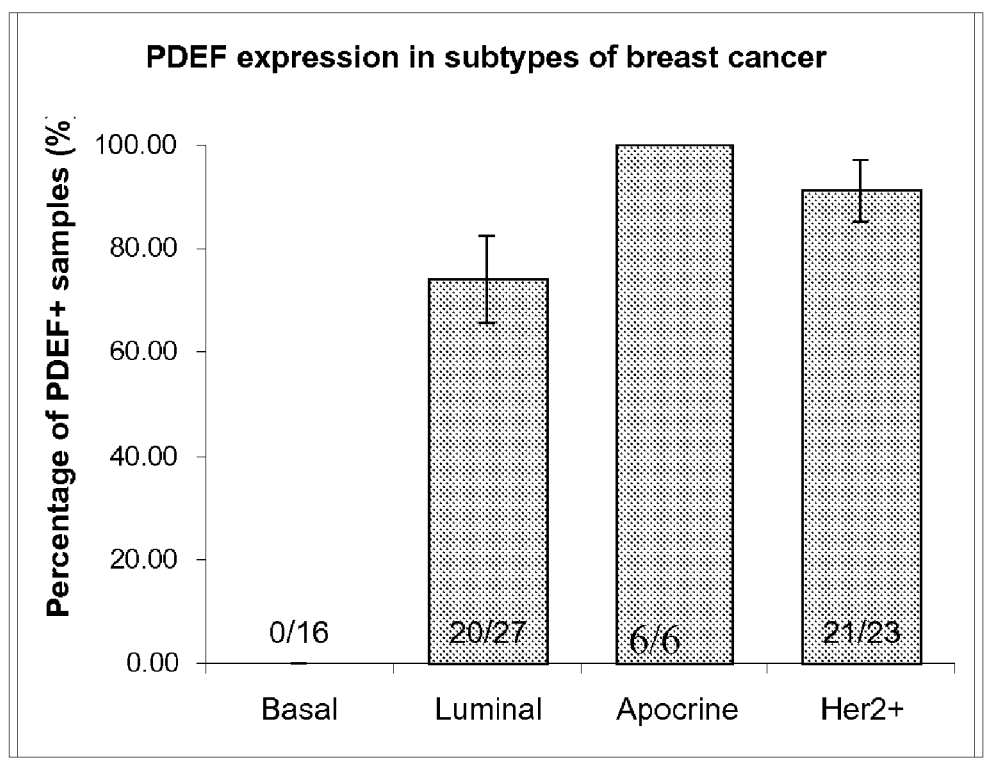
FIG. 11 illustrates PDEF expression in different subtypes of breast cancer. These data were extracted from the gene expression profiling data sets from Minn et al. (13) and Farmer et al. (15). As shown, PDEF was not expressed in any of the 16 tumors of basal subtype. In contrast, 20 of 27 (74%) of luminal tumors; 6 of 6 (100%) of apocrine tumors and 21 of 23 (91%) Her2/neu-positive tumors expressed PDEF. A sample was considered PDEF− positive if majority of the probe sets were scored "present" for PDEF. The error for the proportion is computed with assumption of binomial distribution.

PDEF expression was further examined in existing gene expression datasets (13, 15) to determine PDEF expression characteristics in breast cancer subtypes. As shown in FIG. 11, PDEF expression is specifically restricted to tumors arising in the luminal epithelial lineage. In contrast, basal subtype of breast tumors lacked the expression of PDEF. On the basis of these observations, PDEF over expression appears to be linked to the pathogenesis of the luminal subtype of breast cancers that comprise more that 80% of the newly diagnosed breast cancers.

Example 13

High PDEF Expression Correlates with Intermediate to High Gleason Score in Prostate Cancer A Gleason score is given to prostate cancer based upon its microscopic appearance. Cancers with a higher Gleason score are more aggressive and have a worse prognosis. To determine any correlation of PDEF expression with Gleason Score (GS), low, intermediate, or high GS were assigned to prostate carcinomas according to the published criteria, and any relationship between their GS and PDEF expression status were analyzed. It was found that prostate cancers with intermediate GS showed the highest correlation with PDEF expression, i.e., 77/159 (48%) tumors positive for PDEF. In contrast, 24% (11/45) of high GS but only 15% (4/26) of low GS prostate carcinomas were positive for PDEF. Combining intermediate and high GS tumors as one group (n=204), and comparing them with low GS tumors as another group (n=26), 43% (88/204) of intermediate to high grade v/s and 15% (4/26) of low grade prostate carcinomas were positive for PDEF, which was statistically significant (P<0.01).

Example 14

Figure 12:
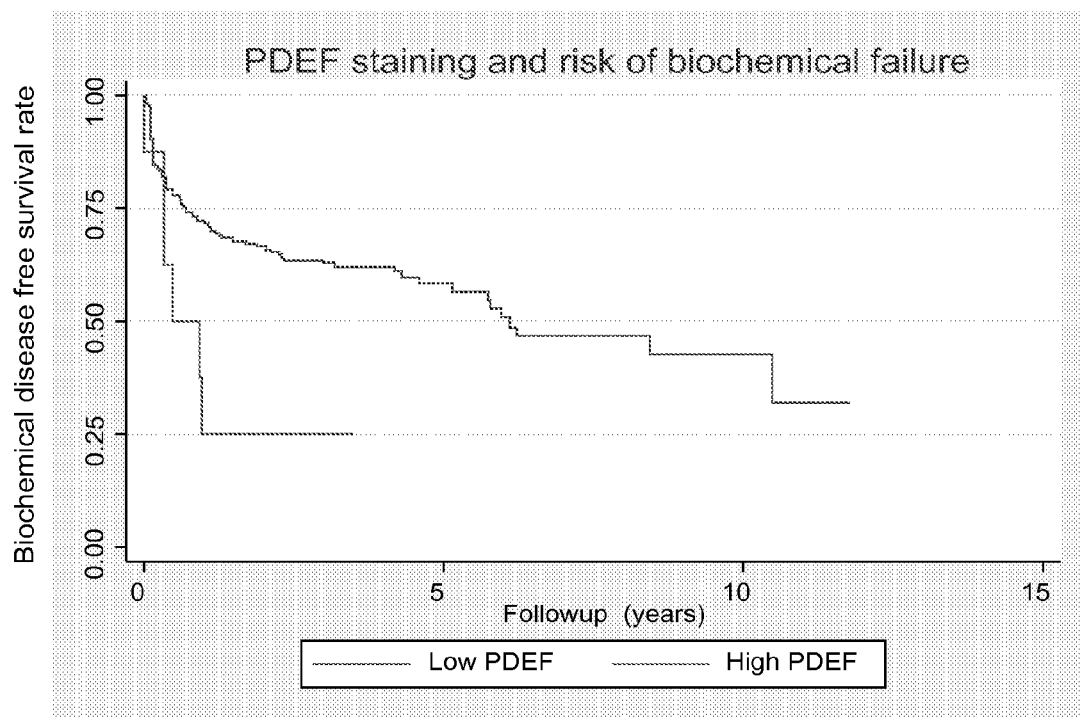
FIG. 12 illustrates that high PDEF expression correlates with biochemical PSA failure. PDEF staining score (0-316) was determined as a product of staining intensity and percentage of positively stained cells in a sample. A cut off value of 180 staining score stratified patients into high and low PDEF categories.

High PDEF Expression Also Shows Correlation with Biochemical PSA Failure in Prostate Cancer Patients Biochemical PSA failure is defined as three consecutive rises of PSA and is used as a surrogate end point indicative of disease recurrence and progression in patients. To determine whether high PDEF expression in prostate tumors predicts PSA failure, patients from a study cohort for whom consecutive PSA readings were available were selected. Specifically, patients with localized prostate cancer treated with radical prostatectomy were included in the study. PDEF expression was scored for staining intensity (+1, +2, +3) and percentage of staining cells. Product of the two indicators (staining score) was used for data analysis and tested for correlation with clinical information. This analysis identified a group of patients with high PDEF expression who have an increased risk for biochemical failure (FIG. 12; p=0.0472). In a multivariate analysis, high PDEF staining score was a predictor of biochemical failure that was independent of preoperative PSA, Gleason sum, pathologic stage, and PDEF expression in the adjacent benign prostate. Together, these data support a role for PDEF in prostate cancer progression as well, and underscore its potential as a novel prognostic/predictive marker in prostate cancer and a target for developing novel therapeutics against this cancer.

Example 15

PDEF as a Vaccine Against Breast and Ovarian Cancers

Due to primarily prostate limited expression of PDEF in normal human tissues, it was hypothesized that males would exhibit tolerance to PDEF. In contrast, females will mount a stronger immune response against PDEF, which should make PDEF a highly desirable vaccine against female cancers, including breast and ovarian cancers. This hypothesis was tested in mice and the results are shown below.

Pse Can Induce Specific Immunity in Female Mice but Weak Immunity in Male Mice

Briefly, groups of FVB female and male mice were immunized with Pse plasmid transfected dendritic cells (Pse-DC). As a positive control, groups of mice were also immunized with Her2/neu plasmid transfected DC (Her2/neu-DC), and additional groups as a negative control were immunized with vector plasmid transfected DC (vector-DC). Specific T cell responses elicited in FVB male and female mice were analyzed by ELIspot assay and representative data from two separate experiments are shown in FIG. 13.

Figure 13A:
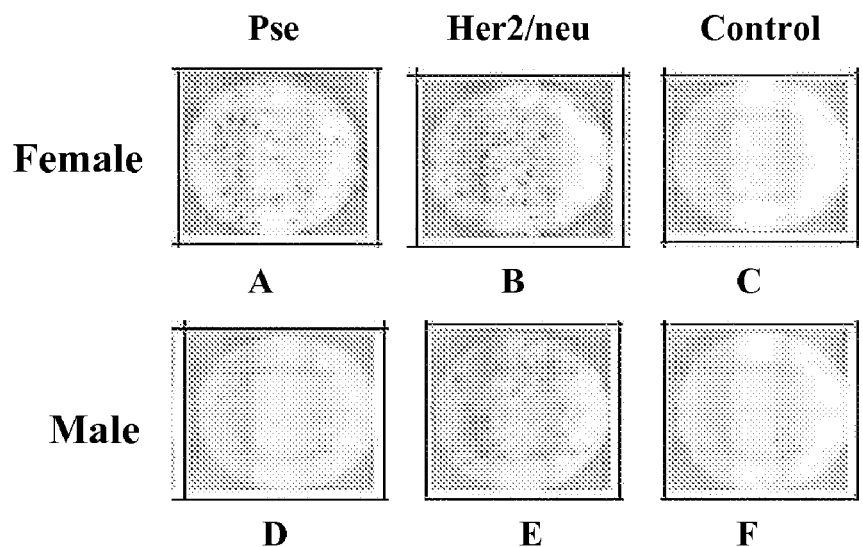
FIG. 13A illustrates a representative experiment showing Pse specific T cell immunity by ELISPOT assay for cytokine IFN-γ. Upper panels A, B and C respectively show representative images of individual wells showing IFN-γ secreting T cells/500,000 splenocytes from Pse-immunized (A); human Her2/neu-immunized (B) and vector-immunized (C) female mice. The lower panels D, E and F, respectively, show data for similarly immunized male mice.
Figure 13B:
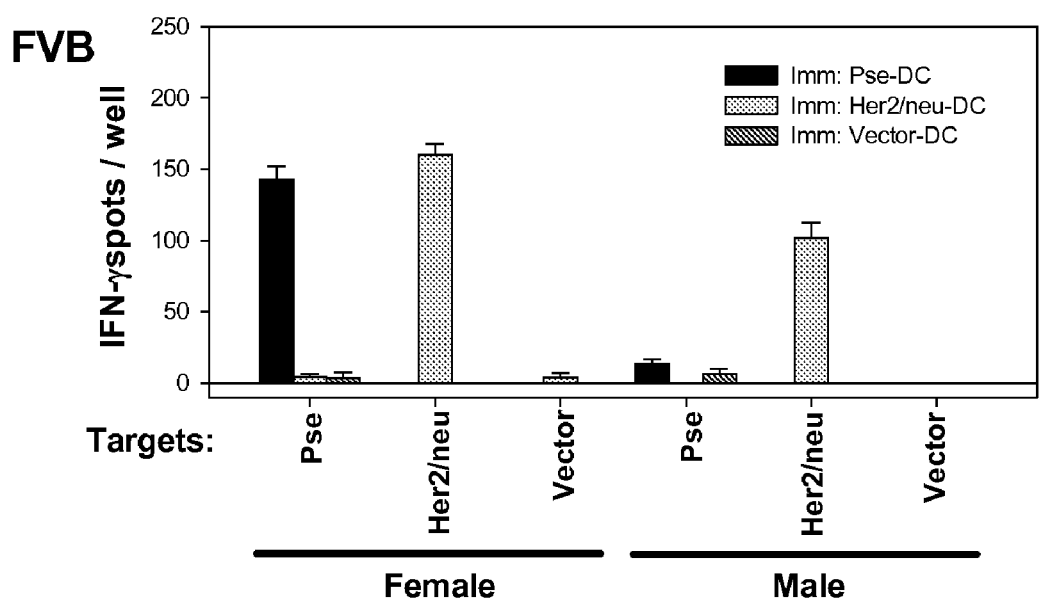
FIG. 13B illustrates quantitative Pse-specific T cell responses in FVB mice. Spleens were harvested from female and male mice following immunization (3 times at two-week interval) with Pse-DC, Her2/neu-DC or Vector-DC respectively. Splenocytes were cultured for 5 days in the presence of respective stimulators and IL-2. The number of Pse-specific IFN-γ secreting T cells was determined by ELIspot assay using Pse-DC, Her2/neu-DC and Vector-DC as target cells.

The data in FIG. 13 show preferential immunogenicity of Pse in female mice since male mice show barely detectable levels of T cell response against Pse. The latter measurement is not due to general lack of responsiveness of male mice, since T cell response to Her2/neu was found to be quite efficient, although relatively lower in comparison to female mice.

Figure 14:
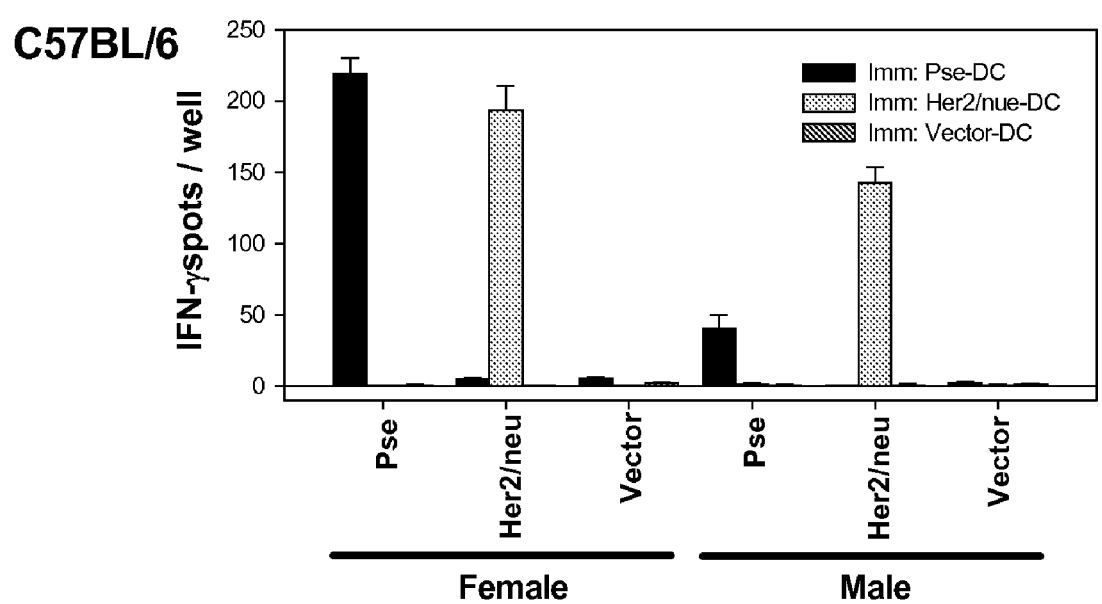
FIG. 14 illustrates quantitative Pse-specific T cell responses in C57BL mice. Spleens were harvested from female and male mice following immunization (3 times at two-week interval) with Pse-DC, Her2/neu-DC or Vector-DC respectively. Splenocytes were cultured for 5 days in the presence of respective stimulators and IL-2. The number of Pse-specific and IFN-γ secreting T cells was determined by ELIspot assay using Pse-DC, Her2/neu-DC and Vector-DC as target cells.

To determine whether the preferential immunogenicity of Pse in female mice is not specific to the FVB strain of mice, identical experiments in the C57BL/6 strain of mice were performed. The data are shown in FIG. 14. Overall, the results are quite similar to those seen in FVB mice, except that the responses of C57BL/6 mice are generally more robust than FVB mice for both male and female mice. Nevertheless, the response of male mice to Pse remains much more muted than that of the female mice.

In summary, the results shown in FIGS. 13 and 14 are highly novel and interesting and Pse is the first example known hereby of a putative breast tumor antigen that shows preferential immunogenicity in female mice. These data strongly suggest that PDEF will be similarly immunogenic in breast cancer patients and support the development of PDEF-based vaccines for treatment of breast cancer in accordance with the present invention.

REFERENCES CITED

Citation of a reference herein shall not be construed as an admission that such reference is prior art to the present invention. All references cited herein are hereby incorporated by reference in their entirety. Below is a listing of references cited herein with reference number indicators:

1. Sood A K, Saxena R, Groth J, Desouki M M, Cheewakriangkrai C, Rodabaugh K J, Kasyapa C S, Geradts J. Expression characteristics of prostate-derived Ets factor support a role in breast and prostate cancer progression. Hum Pathol. 2007; 38:1628-38.
2. Rodabaugh K J, Mhawech-Fauceglia P, Groth J, Lele S, Sood A K. Prostate-derived Ets factor is overexpressed in serous epithelial ovarian tumors. Int J Gynecol Pathol. 2007; 26.10-5.
3. Ghadersohi A, Sood A K. Prostate epithelium-derived Ets transcription factor mRNA is overexpressed in human breast tumors and is a candidate breast tumor marker and a breast tumor antigen. Clin Cancer Res. 2001; 7:2731-8.
4. Nozawa M, Yomogida K, Kanno N, Nonomura N, Miki T, Okuyama A, Nishimune Y, Nozaki M. Prostate-specific transcription factor hPSE is translated only in normal prostate epithelial cells. Cancer Res 2000; 60:1348-52.
5. Feldman R J, Sementchenko V I, Gayed M, Fraig M M, Watson D K. Pdef expression in human breast cancer is correlated with invasive potential and altered gene expression. Cancer Res 2003; 63:4626-31.
6. Ghadersohi A, Pan D, Fayazi Z, Hicks D G, Winston J S, Li F. Prostate-derived Ets transcription factor (PDEF) down-regulates survivin expression and inhibits breast cancer cell growth in vitro and xenograft tumor formation in vivo. Breast Cancer Res Treat. 2007; 102:19-30.
7. Ghadersohi A, Odunsi K, Zhang S, Azrak R G, Bundy B N, Manjili M H, Li F. Prostate-derived Ets transcription factor as a favorable prognostic marker in ovarian cancer patients. Int J. Cancer. 2008; 123:1376-84.
8. Rhodes D R, Kalyana-Sundaram S, Mahavisno V, Varambally R, Yu J, Briggs B B, Barrette T R, Anstet M J, Kincead-Beal C, Kulkami P, Varambally S, Ghosh D, Chinnaiyan A M. Oncomine 3.0: genes, pathways, and networks in a collection of 18,000 cancer gene expression profiles. Neoplasia. 2007; 9:166-80.
9. Chin K, DeVries S, Fridlyand J, Spellman P T, Roydasgupta R, Kuo W L, Lapuk A, Neve R M, Qian Z, Ryder T, Chen F, Feiler H, Tokuyasu T, Kingsley C, Dairkee S, Meng Z, Chew K, Pinkel D, Jain A, Ljung B M, Esserman L, Albertson D G, Waldman F M, Gray J W. Genomic and transcriptional aberrations linked to breast cancer pathophysiologies. Cancer Cell. 2006; 529-41.
10. Miller L D, Smeds J, George J, Vega V B, Vergara L, Ploner A, Pawitan Y, Hall P, Klaar S, Liu E T, Bergh J. An expression signature for p53 status in human breast cancer predicts mutation status, transcriptional effects, and patient survival. Proc Natl Acad Sci USA. 2005; 102:13550-5.
11. Ivshina A V, George J, Senko O, Mow B, Putti T C, Smeds J, Lindahl T, Pawitan Y, Hall P, Nordgren H, Wong J E, Liu E T, Bergh J, Kuznetsov V A, Miller L D. Genetic reclassification of histologic grade delineates new clinical subtypes of breast cancer. Cancer Res. 2006; 66:10292-301.
12. Wang Y, Klijn J G, Zhang Y, Sieuwerts A M, Look M P, Yang F, Talantov D, Timmermans M, Meijer-van Gelder M E, Yu J, Jatkoe T, Berns E M, Atkins D, Foekens J A. Gene-expression profiles to predict distant metastasis of lymph-node-negative primary breast cancer. Lancet. 2005; 365:671-9.
13. Minn A J, Gupta G P, Siegel P M, Bos P D, Shu W, Giri D D, Viale A, Olshen A B, Gerald W L, Massagué J. Genes that mediate breast cancer metastasis to lung. Nature 2005; 436:518-24.
14. Sotiriou C, Wirapati P, Loi S, Harris A, Fox S, Smeds J, Nordgren H, Farmer P, Praz V, Haibe-Kains B, Desmedt C, Larsimont D, Cardoso F, Peterse H, Nuyten D, Buyse M, Van de Vijver M J, Bergh J, Piccart M, Delorenzi M. Gene expression profiling in breast cancer: understanding the molecular basis of histologic grade to improve prognosis. J Natl Cancer Inst. 2006; 98:262-72.

15. Farmer P, Bonnefoi H, Becette V, Tubiana-Hulin M, Fumoleau P, Larsimont D, Macgrogan G, Bergh J, Cameron D, Goldstein D, Duss S, Nicoulaz A L, Brisken C, Fiche M, Delorenzi M, Iggo R. Identification of molecular apocrine breast tumours by microarray analysis. Oncogene. 2005; 24:4660-71.

16. Tjensvoll K, Gilje B, Oltedal S, Shammas V F, Kvaløy J T, Heikkilä R, Nordgård O. A small subgroup of operable breast cancer patients with poor prognosis identified by quantitative real-time RT-PCR detection of mammaglobin A and trefoil factor 1 mRNA expression in bone marrow. Breast Cancer Res Treat. 2008 Oct. 10. [Epub ahead of print]

17. Sorlie T, Tibshirani R, Parker J, Hastie T, Marron J S, Nobel A, Deng S, Johnsen H, Pesich R, Geisler S, Demeter J, Perou C M, Lønning P E, Brown P O, Børresen-Dale A L, Botstein D. Repeated observation of breast tumor subtypes in independent gene expression data sets. Proc Natl Acad Sci USA. 2003; 100:8418-23

18. Sood A K, Peng L and Kasyapa C. Personal communication regarding unpublished data.

19. Oettgen P, Finger E, Sun Z, Akbarali Y, Thamrongsak U, Boltax J, Grall F, Dube A, Weiss A, Brown L, Quinn G, Kas K, Endress G, Kunsch C, Libermann T A. PDEF, a novel prostate epithelium-specific ets transcription factor, interacts with the androgen receptor and activates prostate-specific antigen gene expression. J Biol Chem. 2000; 75:1216-25.

20. Gu X, Zerbini L F, Otu H H, Bhasin M, Yang Q, Joseph M G, Grall F, Onatunde T, Correa R G, Libermann T A. Reduced PDEF expression increases invasion and expression of mesenchymal genes in prostate cancer cells. Cancer Res. 2007; 67:4219-26.

21. Ghadersohi, A., Odunsi K, Lele S, Collins Y, Greco, W R, Winston J, Liang, P, Sood, A K. Prostate-derived Ets factor shows better tumor-association than other cancer-associated molecules. Oncol. Rep. 2004; 11:453-458.

22. Galang C K, Muller W J, Foos G, Oshima R G, Hauser C A. Changes in the expression of many Ets family transcription factors and of potential target genes in normal mammary tissue and tumors. J Biol Chem 2004; 279:11281-92.

23. He J, Pan Y, Hu J, Albarracin C, Wu Y, Le Dai J. Profile of Ets Gene Expression in Human Breast Carcinoma. Cancer Biol Ther. 2007; 6: 76-82.

24. Marchionni L, Wilson R F, Wolff A C, Marinopoulos S, Parmigiani G, Bass E B, Goodman S N. Systematic review: gene expression profiling assays in early-stage breast cancer. Ann Intern Med. 2008; 148:358-69.

25. Paik S, Shak S, Tang G, Kim C, Baker J, Cronin M, Baehner F L, Walker M G, Watson D, Park T, Hiller W, Fisher E R, Wickerham D L, Bryant J, Wolmark N. A multigene assay to predict recurrence of tamoxifen-treated, node-negative breast cancer. N Engl J. Med. 2004; 351:2817-26.

26. van't Veer L J, Dai H, van de Vijver M J, He Y D, Hart A A, Mao M, Peterse H L, van der Kooy K, Marton M J, Witteveen A T, Schreiber G J, Kerkhoven R M, Roberts C, Linsley P S, Bernards R, Friend S H. Gene expression profiling predicts clinical outcome of breast cancer. Nature. 2002; 415:530-6.

A1. Oettgen P, Finger E, Sun Z, Akbarali Y, Thamrongsak U, Boltax J, Grall F, Dube A, Weiss A, Brown L, Quinn G, Kas K, Endress G, Kunsch C, Libermann T A. PDEF, a novel prostate epithelium-specific ets transcription factor, interacts with the androgen receptor and activates prostate-specific antigen gene expression. J Biol Chem. 2000; 75:1216-25.

A2. Ghadersohi A, Sood A K. Prostate epithelium-derived Ets transcription factor mRNA is overexpressed in human breast tumors and is a candidate breast tumor marker and a breast tumor antigen. Clin Cancer Res. 2001; 7:2731-8.

A3. Turcotte S, Forget M A, Beauseigle D, Nassif E, Lapointe R. Prostate-derived Ets transcription factor overexpression is associated with nodal metastasis and hormone receptor positivity in invasive breast cancer. Neoplasia. 2007; 9:788-96.

A4. Feldman R J, Sementchenko V I, Gayed M, Fraig M M, Watson D K. Pdef expression in human breast cancer is correlated with invasive potential and altered gene expression. Cancer Res. 2003; 63 :4626-31.

A5. Nozawa M, Yomogida K, Kanno N, Nonomura N, Miki T, Okuyama A, Nishimune Y, Nozaki M. Prostate-specific transcription factor hPSE is translated only in normal prostate epithelial cells. Cancer Res. 2000 Mar. 1; 60(5):1348-52.

A6. Sood A K, Saxena R, Groth J, Desouki M M, Cheewakriangkrai C, Rodabaugh K J, Kasyapa C S, Geradts J. Expression characteristics of prostate-derived Ets factor support a role in breast and prostate cancer progression. Hum Pathol. 2007; 38:1628-38.

A7. Ghadersohi A, Pan D, Fayazi Z, Hicks D G, Winston J S, Li F. Prostate-derived Ets transcription factor (PDEF) downregulates survivin expression and inhibits breast cancer cell growth in vitro and xenograft tumor formation in vivo. Breast Cancer Res Treat. 2007; 102:19-30.

A8. Ghadersohi A, Odunsi K, Zhang S, Azrak R G, Bundy B N, Manjili M H, Li F. Prostate-derived Ets transcription factor as a favorable prognostic marker in ovarian cancer patients. Int J. Cancer. 2008; 123:1376-84.

B1. Bray F, McCarron P, Parkin D M. The changing global patterns of female breast cancer incidence and mortality. Breast Cancer Res 2004; 6:229-39.

B2. Chew H K. Medical management of breast cancer: today and tomorrow. Cancer Biother Radiopharm 2002; 17:137-49.

B3. Ward J F, Moul J W. Biochemical recurrence after definitive prostate cancer therapy. Part I: defining and localizing biochemical recurrence of prostate cancer. Curr Opin Urol 2005; 15:181-86.

B4. Ward J F, Moul J W. Biochemical recurrence after definitive prostate cancer therapy. Part II: treatment strategies for biochemical recurrence of prostate cancer. Curr Opin Urol 2005; 15:187-95.

B5. Ryan C J, Small E J. Progress in detection and treatment of prostate cancer. Curr Opin Oncol 2005; 17:257-60.

B6. Jemal A, Tiwari R C, Murray T, et al. American Cancer Society. Cancer statistics, 2004. CA Cancer J Clin 2004; 54:8-29.

B7. Auersperg N, Ota T, Mitchell G W. Early events in ovarian epithelial carcinogenesis: progress and problems in experimental approaches. Int J Gynecol Cancer 2002; 12:691-703.

B8. See H T, Kavanagh J J, Hu W, et al. Targeted therapy for epithelial ovarian cancer: current status and future prospects. Int J Gynecol Cancer 2003; 13:701-734.

B9. Oettgen P, Finger E, Sun Z, Akbarali Y, Thamrongsak U, Boltax J, Grall F, Dube A, Weiss A, Brown L, Quinn G, Kas K, Endress G, Kunsch C, Libermann T A. PDEF, a novel prostate epithelium-specific ets transcription factor, interacts with the androgen receptor and activates prostate-specific antigen gene expression. J Biol Chem 2000; 275: 1216-25.

B10. Sharrocks A D. The ETS-domain transcription factor family. Nat Rev Mol Cell Biol 2001; 2:827-37.

B11. Mimeault M. Structure-function studies of ETS transcription factors. Crit Rev Oncog 2000; 11:227-53.

B12. Verger A, Duterque-Coquillaud M. When Ets transcription factors meet their partners. Bioessays 2002; 24:362-70.

B13. Gunawardane R N, Sgroi D C, Wrobel C N, Koh E, Daley G Q, Brugge J S. Novel role for PDEF in epithelial cell migration and invasion. Cancer Res 2005; 65:11572-80.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A vaccine for treating or immunizing a female individual against a cancer disease associated with positive PDEF expression, said vaccine comprising:
    (a) dendritic cells transfected with a viral or plasmid expression vector comprising a nucleotide sequence that is operably linked to a promoter and that encodes an antigen effective to induce T cell immunity that inhibits growth of tumor cells that express PDEF, wherein said tumor cells correspond to a female cancer disease that is associated with positive PDEF expression, wherein said antigen comprises the amino acid sequence of SEQ ID NO:1; and
    (b) an adjuvant.

* * * * *